US008476402B2

(12) United States Patent
Williams et al.

(10) Patent No.: US 8,476,402 B2
(45) Date of Patent: Jul. 2, 2013

(54) CARBOHYDRATE LACTONE POLYMERS

(75) Inventors: Charlotte K. Williams, London (GB);
Molly Morag Stevens, London (GB);
Min Tang, London (GB)

(73) Assignee: Imperial Innovations Limited, London (GB)

( * ) Notice: Subject to any disclaimer, the term of this patent is extended or adjusted under 35 U.S.C. 154(b) by 232 days.

(21) Appl. No.: 12/934,719

(22) PCT Filed: Mar. 27, 2009

(86) PCT No.: PCT/GB2009/000825
§ 371 (c)(1),
(2), (4) Date: Dec. 7, 2010

(87) PCT Pub. No.: WO2009/118538
PCT Pub. Date: Oct. 1, 2009

(65) Prior Publication Data
US 2011/0077380 A1    Mar. 31, 2011

(30) Foreign Application Priority Data
Mar. 28, 2008   (GB) .................................. 0805701.0

(51) Int. Cl.
C08G 63/08    (2006.01)
C08G 63/64    (2006.01)
C08G 63/82    (2006.01)
A61L 17/00    (2006.01)
A61L 31/00    (2006.01)
C07D 309/30   (2006.01)

(52) U.S. Cl.
USPC ........... 528/354; 528/357; 528/358; 525/415; 549/292; 606/230; 606/231

(58) Field of Classification Search
USPC ........... 528/354, 355, 356, 357, 358; 549/292
See application file for complete search history.

(56) References Cited

U.S. PATENT DOCUMENTS
3,301,825 A *   1/1967  Hostettler et al. ............. 528/354
5,480,580 A *   1/1996  Sakashita et al. ........ 252/299.61
2001/0039327 A1* 11/2001 Minami ........................ 528/354

FOREIGN PATENT DOCUMENTS
EP          0388225 A2      9/1990
JP          2002-167430     6/2002

OTHER PUBLICATIONS

Tang et al (Biomaterials from sugars: ring-opening polymerization of a carbohydrate lactone, Chem. Commun., 2009, 941-943, published on web Dec. 18, 2008).*
Nelson, Charles R. et al: "The Conversion of D-Glucono-1,5-Lactone Into an a-Pyrone Derivative"; Carbohydrate Research, 60 (1978), 267-273.
Pedersen, Christian: "Improved preparation and synthetic uses of 3-deoxy-D-arabino-hexonolactone: an efficient synthesis of Leptosphaerin"; Carbohydrate Research 315 (1999), 192-197.
Williams, Charlotte K.: "Synthesis of functionalized biodegradable polyesters"; Chemical Society Reviews 2007, 36, 1573-1580.

(Continued)

Primary Examiner — Randy Gulakowski
Assistant Examiner — Rachel Kahn
(74) Attorney, Agent, or Firm — Lathrop & Gage LLP; Brian C. Trinque

(57) ABSTRACT

The present invention relates to a novel carbohydrate lactone, functionalized aliphatic polyesters and copolymers formed therefrom, and processes for the preparation thereof from renewable resources.

33 Claims, 9 Drawing Sheets

OTHER PUBLICATIONS

Zamora, Francisca et al.: "Synthesis of 3-deoxy-2,4-di-O-methyl-D-erythro-pentono-1,5-lactone and of its L enantiomer by stereoselective hydrogenation of a,b-unsaturated aldono-1,5-lactones"; Carbohydrate Research 293 (1996), 251-258.

Breyfogle, Laurie E. et al., "Comparison of structurally analogous Zn2, Co2, and MG2 catalysts for the polymerization of cyclic esters," Dalton Transactions, vol. 7:928-936 (2006).

Carothers, Wallace H. et al., "Studies of Polymerization and Ring Formation. X. The Reversible Polymerization of Six-membered Cyclic Esters," J. Am. Chem. Soc., vol. 54:761-772 (1932).

Drew, Harry Dugald Keith et al., "CXII. Studies in Polymerisation. Part I. 2:3:4-Trimethyl 1-Arabonolactone," J. Chem. Soc., pp. 775-779 (1927).

Haider, Anita F. et al., "Synthesis of Highly Functionalized Oligo- and Copolyesters from a Carbohydrate Lactone," Journal of Polymer Science Part A: Polymer Chemistry, vol. 46(8):2891-2896 (2008).

Kumar, Rajesh et al., "Functionalized Polylactides: Preparation and Characterization of [L]-Lactide-co-Pentofuranose," Macromolecules, vol. 35:6835-6844 (2002).

Liu, Xiaobo et al., "Kinetics of thermo-oxidative and thermal degradation of poly(D,L-lactide) (PDLLA) at processing temperature," Polymer Degradation and Stability, vol. 91:3259-3265 (2006).

Marcincinova-Benabdillah, Katarina et al., "Novel Degradable Polymers Combining D-Gluconic Acid, a Sugar of Vegetal Origin, with Lactic and Glycolic Acids," Biomacromolecules, vol. 2:1279-1284 (2001).

Pinilla, Immaculada Molina et al., "Synthesis of 2,3,4,5-tetra-O-methyl-D-glucono-1,6-lactone as a monomer for the preparation of copolyesters," Carbohydrate Research, vol. 338:549-555 (2003).

Varela, Oscar J. et al., "Beta-Elimination in Aldonolactones, Synthesis of 3,6-Dideoxy-L-arabino-Hexose (Ascarylose)," Carbohydrate Research, vol. 70:27-35 (1979).

Williams, Charlotte K. et al., "A Highly Active Zinc Catalyst for the Controlled Polymerization of Lactide," J. Am. Chem. Soc., vol. 125:11350-11359 (2003).

International Search Report for Application No. PCT/GB2009/000825, dated Oct. 26, 2009.

* cited by examiner

CARBOHYDRATE LACTONE POLYMERS

This application is a 35 U.S.C. §371 filing of International Application Number PCT/GB2009/000825 which was filed on Mar. 27, 2009, which claims priority to Great Britain Application 0805701.0, which was filed on Mar. 28, 2008. The entire contents of the aforementioned applications are hereby incorporated herein by reference. The contents of any patents, patent applications, and references cited throughout this specification are hereby incorporated by reference in their entireties.

The present invention relates to a novel carbohydrate lactone, functionalized aliphatic polyesters and copolymers formed therefrom, and processes for the preparation thereof from renewable resources.

Renewable resources, in particular biomass (material derived from biological sources), are an attractive alternative to petrochemicals for use in many applications, for example for use as raw materials for chemical and polymer production. Renewal resources seek to overcome problems with petrochemical supply, cost, environmental impact and sustainability. Further, bioderived materials can often be biocompatible, bioresorbable and even biodegradable. One such bioderived material is polylactide, produced by ring-opening polymerization of lactic acid, which itself is derived from biomass such as corn or sugar beet. Polylactide has good mechanical and physical properties and is used to manufacture packaging materials, as well as specialized medical articles. Polylactide thus highlights the potential of biomass as a more environmentally sound and sustainable alternative to the use of petrochemicals for polymer production. However, polylactide has a high glass transition temperature (Tg) and lacks chemical functional groups, resulting in it being hydrophobic and slow to degrade, which limits its applications and complicates its disposal. Moreover, for certain applications, polylactide is not suitable due to its high crystallinity, brittleness, lack of total absorption and thermal instability.

Functionalized aliphatic polyesters could seek to address the limitations of polylactide. However, functionalized aliphatic polyesters are currently not widely available. The ring-opening polymerization of functionalized lactones is an appealing route for the preparation of funtionalized aliphatic polyesters because it can be well controlled. Previous reports addressing the preparation and polymerization of functionalized lactones have been hampered by complex, multi-step lactone syntheses and moderate yields. Moreover, in these previous attempts the lactone monomer ring strain is insufficient to produce polymers. In these examples, the functionalized lactone monomers are copolymerized with high strain rings, meaning that the incorporation of functional groups in the resulting copolymer is low (Marcincinova-Benabdillah et al, Biomacromolecules 2001, 2, 1279-1284 relating to 1,4-dioxane-2,5-diones substituted at position 3 with protected D-gluconic acids; Kumar et al, Macromolecules 2002, 35, 6835-6844, relating to tetra-O-methyl-D-glucono-1,6-lactone; and Pinilla et al, Carbohydr. Res. 2003, 338, 549-555 relating to cyclic carbonate monomers derived from D-xylose). Furthermore, there are very few examples of the ring-opening polymerization of functionalized lactones derived from renewable resources.

Carbohydrate 1,5-lactones have potential as attractive monomers for ring opening polymerization, being derivable from renewable resources, inexpensive and safe (of low toxicity). However, references to their polymerization are very limited. In 1927, Haworth observed that tri-O-methyl-D-arabino-1,5-lactone, when left for some weeks in a closed vessel containing a trace of acetyl chloride vapour, reacted to form a solid, apparently amorphous mass, termed a 'polymeride' (Drew, H. D. K. et al, J. Chem. Soc. 1927, 775-779). Decades later the production of a tetra (2-, 3-, 4-, 6-) substituted D-gluconolactone from D-glucose produced from starch and its ring-opening polymerization catalyzed by a metal-complex was reported (JP 2002167430). In both reports, product characterization is limited. Moreover, recent work has highlighted limitations to the polymerization of tetra (2-, 3-, 4-, 6-) substituted D-gluconolactones. Specifically, attempts to polymerize tetra-O-acetyl-D-gluconolactone did not succeed, but instead led, at best, to the production of a trimer (Haider and Williams, J. Polymer. Sci 2008, 46(8), 2891-2896). Moreover, many metal complexes (e.g. those based on zinc or aluminium compounds) led to decomposition of the lactone rather than to polymerization. It was only when using a tin catalyst that trimerisation was achieved and the product of the trimerisation was not stable in the presence of the tin species. Tetra-O-methyl-D-gluconolactone was also found to undergo decomposition in the presence of metal complexes.

There is therefore a need in the art for an improved process for the production of bioderived polymers from renewable resources enabling the production of polymers which have low glass transition temperatures and are rapidly degradable. Accordingly, this invention provides a functionalized lactone compound which can be produced from readily available carbohydrates and can undergo a controlled ring-opening polymerization reaction to form a functionalized polyesters or copolyesters useful as a bioderived polymer.

Accordingly, in a first aspect the present invention provides a polymer formed from monomers, wherein the monomers comprise a lactone compound of formula (I)

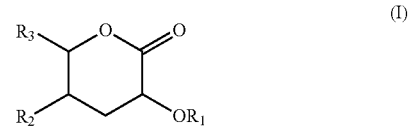

wherein $R_1$ is selected from hydrogen, alkyl, haloalkyl, acyl, ester, aryl, heteroaryl, alkylaryl, alkylheteroaryl, silyl, sulfonyl, a drug molecule or a peptide;

$R_2$ is hydrogen or $OR_{1'}$; and $R_3$ is methyl or —$CH_2OR_{1''}$;

wherein $R_{1'}$, and $R_{1''}$ are both as defined for $R_1$ and each occurrence of $R_1$, $R_{1'}$ and $R_{1''}$ may be the same or different.

Preferably, alkyl is Me, Et or iPr; alkylaryl is benzyl; acyl is —$C(O)CH_3$ or —$C(O)CF_3$; ester is —$C(O)O^tBu$ or —$C(O)OC_{15}H_{11}$ (Fmoc); aryl is phenyl; silyl is $SiMe_3$; and sulfonyl is tosyl ($C_7H_7SO_2$).

Preferably, when $R_3$ is methyl, $R_2$ is not $OR_{1'}$.

In a preferred embodiment, $R_2$ is hydrogen and $R_3$ is —$CH_2OR_{1''}$. Preferably, $R_1$ and $R_{1''}$ are acyl. More preferably, $R_1$ is —$C(O)CH_3$; $R_2$ is hydrogen and $R_3$ is —$CH_2OC(O)CH_3$.

In another preferred embodiment, $R_2$ is hydrogen and $R_3$ is methyl. Preferably, $R_1$ is acyl. More preferably, $R_1$ is —$C(O)CH_3$.

In yet another preferred embodiment, $R_2$ is $OR_{1'}$ and $R_3$ is —$CH_2OR_{1''}$. Preferably, $R_1$, $R_{1'}$ and $R_{1''}$ are acyl. More preferably, $R_1$, $R_{1'}$ and $R_{1''}$ are —$C(O)CH_3$.

The polymerization reaction occurring between lactone monomers of formula (I) may be an equilibrium reaction which can lead to the formation of both linear polymers and cyclic polymers (macrocycles). It has been determined that once the polymerization of a lactone compound of the invention has reached equilibrium, the proportion of cyclic polymer is greater than the proportion of linear polymers in the mixture, with the exact proportion of cyclic vs. linear polymer depending on the % conversion of monomer to polymer. Linear polymers and cyclic polymers can be separated by fractionation using solvents. This enables isolation of the cyclic polymer as a precipitate.

Thus, in a preferred embodiment the polymer is provided as a mixture of a cyclic polymer and a linear polymer, wherein the cyclic and linear polymers have the structures set out below:

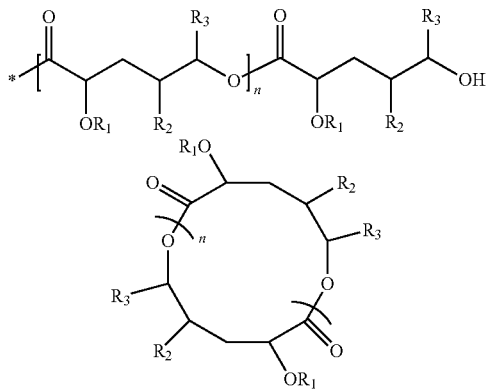

wherein n is between 1 and 60 and wherein $R_1$, $R_2$ and $R_3$ are as defined above and wherein termination of the linear polymer as represented by * is OH or OR, wherein R is alkyl or alkylaryl. The OR end group may be provided by a polymerisation initiator used in the polymerization process to form the polymer.

In a preferred embodiment, the mixture comprises a greater proportion of cyclic polymer than linear polymer (on a % weight basis).

Preferably, the polymer has a Mn of 700 to 13,000. In certain embodiments, the polymer has an Mn from 5,000 to 13,000. In other embodiments, the polymer is an oligomeric product having an Mn from 700 to 800.

In another embodiment, the invention provides the isolated cyclic polymer. For the cyclic polymer n is preferably between 3 and 24 (for example 7).

In another embodiment, the invention provides the linear polymer of formula:

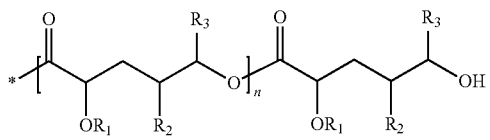

wherein n is from 1 to 60, preferably from 3 to 60.

Advantageously, cyclic polymers tend to have lower glass transition temperatures and could be useful for blending with other polymers (as plasticizers).

The ring-opening polymerization is well controlled. This is demonstrated by an observed linear increase in $M_n$ (molecular weight) with the degree of polymerization and narrow polydispersity indices (PDIs). Controlled polymerization is important for applications of the bioderived polymers because it enables accurate prediction of the $M_n$ and properties of the polymer from the stoichiometry of the polymerization reaction.

The polymer of the invention may be a homopolymer, wherein the homopolymer is derived from monomers, the monomers being a lactone compound of formula (I). Alternatively, the polymer may be a copolymer formed from one or more lactone monomers of formula (I) and one or more other monomers.

Thus, in a further embodiment, the polymer of the invention is a copolymer formed from a lactone compound of the invention and a known lactone or a cyclic carbonate, preferably selected from lactide, glycolide, caprolactone, valerolactone, butyrolactone and trimethylene carbonate. Preferably, the copolymer is a block copoly(ester) or a random copoly(ester).

The copolymer can be represented by the formula:

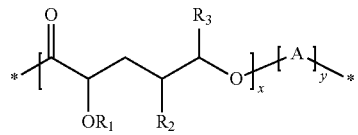

wherein the mole fraction of x is between 0.5% and 20% and the mole fraction of y is between 80% and 99.5%, wherein $R_1$, $R_2$ and $R_3$ are as defined in respect of the first aspect of the invention.

It will be appreciated that the copolymer may be random copolymer (i.e. made up by random repetitions of the x and y repeat units) or a block copolymer (comprising linked homopolymer subunits i.e. a subunit comprising x monomers and a subunit comprising y monomers).

Preferably, the polymer is a copolymer formed from a lactone compound of formula (I) as defined herein and lactide (R-lactide, S-lactide, meso-lactide (R,S-lactide) and rac-lactide, more preferably S-lactide or rac-lactide. Such a copolymer can be represented by the following formula:

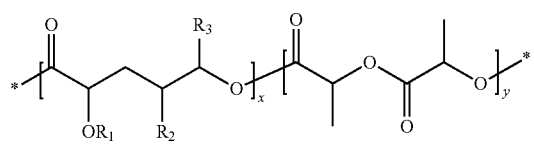

wherein the mole fraction of x within the random copolymer is between 0.5% and 20% and the mole fraction of y is between 80% and 99.5%, wherein $R_1$, $R_2$ and $R_3$ are as defined above in respect of the first aspect of the invention and wherein termination of the copolymer as represented by * is OH at the oxo end (right-hand end of the structure shown above) and OR at the carbonyl end, wherein R is alkyl or alkylaryl. The OR end group may be provided by a polymerisation initiator used in the polymerization process to form the polymer. Preferably, the copolymer is a random copolymer.

The total monomer repeat within the copolymer, ie total of x plus y, is preferably at least 20, for example, from 20 to 740.

Preferably, the Mn of the copolymer is from 10,000 to 100,000.

Preferably, the loading of the lactone compound within the copolymer is up to 25% (by weight). More preferably, the loading of the lactone compound within the copolymer is from 20% to 25%. The loading can be determined by intergration of a $^1H$ NMR spectrum of the copolymer, specifically for example by dividing integration of polymer peaks arising from ring opened lactone with peaks from the second lactone or cyclic carbonate.

In a further embodiment, the invention provides a graft copolymer comprising a polymer backbone formed from polymerization of a lactone compound of the invention and a second polymer bonded to functional groups present on the lactone monomer. The graft copolymer may be, for example, a graft copolyester, a graft copoly(ester-acrylate) or a graft copoly(ester-peptide).

It will be appreciated that the features of the copolymer embodiments described above where the second lactone is lactide also apply to a copolymer of a lactone compound of formula (I) with a lactone selected from glycolide, caprolactone, valerolactone, butyrolactone or a cyclic carbonate, preferably trimethylene carbonate.

In a second aspect, the present invention provides a process for the polymerization of a lactone compound of formula (I), wherein the process comprises exposing a lactone compound of formula (I) to a metal initiator and allowing a ring opening polymerization reaction to occur.

In a preferred embodiment, the initiator is a Lewis acidic metal alkoxide complex which initiates polymerization by causing ring-opening of the lactone via a corordination insertion mechanism. The lactone coordinates to the Lewis acidic metal alkoxide complex, resulting in the complex activating and attacking the lactone at the carbonyl carbon. Acyl bond cleavage then results in ring opening and generation of a new metal alkoxide species from which the cycle can reinitiate. Preferably, the initiator is selected from the group consisting of tin initiators, including tin(II) alkoxide complexes and tin(II) carboxylate complexes+alcohols (e.g. Sn(II) octanoate and two equivalents of an alcohol or one equivalent of a diol group (e.g. methanol, benzyl alcohol, butanediol) or Sn(OBu)$_2$); zinc alkoxide complexes (including complexes with a ligand and without a ligand (homoleptic complexes)); aluminium alkoxide complexes; titanium alkoxide complexes; zirconium alkoxide complexes; alkali earth alkoxide complexes; yttrium alkoxide complexes; lanthanum alkoxide complexes; and calcium alkoxide complexes.

Preferably, the initiator is a tin alkoxide initiator, for example of formula Sn(OR)$_2$, or a zinc alkoxide complex, for example of formula LZnOR, wherein R is alkyl or alkylaryl and L is a zinc-coordinating ligand. Preferably, R is ethyl, isopropyl, butyl, methyl or benzyl. Thus, the zinc alkoxide complex can comprise, for example, zinc ethoxide, zinc isopropoxide, zinc methoxide or zinc benzyloxide. More preferably, the zinc alkoxide complex is of formula LZnOR, wherein R is alkyl and L is a zinc-coordinating ligand, of formula:

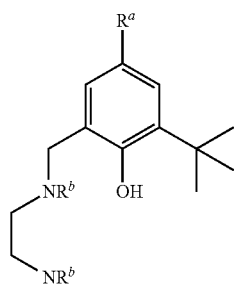

wherein $R^a$ is hydrogen, alkyl (e.g. tBu, Me), alkoxy (e.g. OMe), a halogen (e.g. F, Cl, Br), NO$_2$, NH$_2$, alkylamine or dialkylamine (e.g. NMe$_2$); and each $R^b$ is independently hydrogen, alkyl (e.g. Me, Et, iPr), alkylaryl (e.g. benzyl) or aryl (e.g. Phenyl).

Preferable, $R^a$ is tBu and each occurrence of $R^b$ is Me.

More preferably, the initiator is zinc ethoxide complex having the formula LZnOEt, preferably wherein L has the formula shown above.

Preferably, the polymerisation initiator provides an end group of the polymer, adjacent a carbonyl group of the polymer, thus terminating the polymer with —C(O)OR, OR being provided by the initiator.

Preferably, the polymerization is performed under mild conditions, namely with 0.5M-2M concentration of lactone compound in a chlorinated solvent (e.g CDCl$_3$), an ether solvent (e.g. THF) or an aromatic solvent (e.g. toluene) at a temperature of 25-100° C. Alternatively, the polymerization may be carried out at 25-100° C. with no solvent present.

Preferably, the polymerization is carried out at a 1M concentration of lactone compound in CDCl$_3$ at 25° C.

Advantageously, the use of mild polymerization conditions is beneficial for a commercial process, requiring lower energy input and also facilitating ease of handling and sampling. Moreover, mild polymerization conditions result in significantly less degradation of the polymer than would be seen at harsher conditions (these polymers can be burnt at higher temperatures). Also, as the polymerization is an equilibrium reaction, higher $M_n$ polymer is possible by using lower temperature. Finally, mild conditions such as used here make the incorporation of sensitive molecules (e.g. drugs, peptides, cell growth factors) possible. If the polymerization required harsh conditions then it would not be feasible to include useful but sensitive molecules in the polymer structure.

In a preferred embodiment, the ratio, on a molar basis, of lactone monomer of formula (I):initiator is from 130:1 to 20:1, preferably 130:1 to 30:1, preferably 70:1 to 20:1, more preferably from 65:1 to 30:1.

In a preferred embodiment, the process is a copolymerization process comprising exposing a lactone compound of formula (I) and a second lactone compound or a cyclic carbonate to a metal initiator and allowing copolymerization to occur.

Preferably, the process for copolymerization comprises providing a mixture of a lactone compound of formula (I) with a second lactone compound or a cyclic carbonate, exposing the mixture to a metal initiator and allowing a ring opening polymerization reaction to occur to produce a random copolymer. Preferably the second lactone compound is selected from lactide, glycolide, caprolactone, valerolactone, butyrolactone. Preferably, the cyclic carbonate is trimethylene carbonate. Preferably, the second lactone compound is lactide (R-lactide, S-lactide, meso-lactide (R,S-lactide) or rac-lactide, more preferably S-lactide or rac-lactide).

In another preferred embodiment, the process for copolymerization comprises exposing a lactone compound of formula (I) to a metal initiator and allowing a ring opening polymerization reaction to occur followed by addition of a second lactone compound or a cyclic carbonate, to produce a block copolymer. Preferably the second lactone compound is selected from lactide, glycolide, caprolactone, valerolactone, butyrolactone. Preferably, the cyclic carbonate is trimethylene carbonate. Preferably, the second lactone compound is lactide (R-lactide, S-lactide, meso-lactide (R,S-lactide) or rac-lactide, more preferably S-lactide or rac-lactide).

Where the polymerization process is copolymerization, in a preferred embodiment, the molar ratio of lactone monomer of formula (I):second lactone or cyclic carbonate is from 1:1 to 1:1000.

In a preferred embodiment, the lactone compound of formula (I) is produced according to the process of the third aspect of the invention, as described below.

The invention encompasses polymers as produced by the polymerization process described above.

In a third aspect, the present invention provides a lactone compound of formula (I) as defined above. The lactone compound can be produced from readily available biological sources (carbohydrates) and, thus, the lactone and polymers of the invention can be biomaterials (material derived from biological sources).

In a fourth aspect, the present invention provides a process for the preparation of a lactone compound of formula (I), the process comprising the steps of:
a) reacting a tetra-O-substituted(R)-D-gluconolactone of formula H with a base to form a compound of formula IIIa or IIIb;

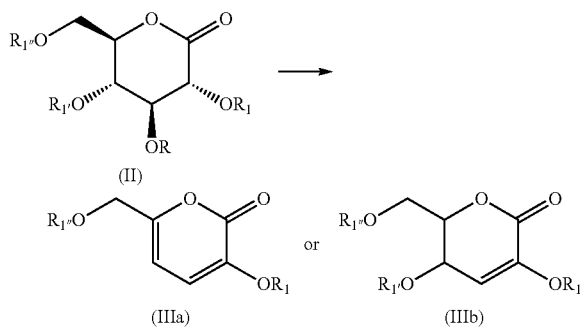

b) optionally further reacting the compound of formula IIIa with a base to form a compound of formula IV; and

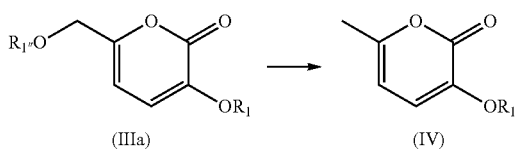

c) reducing the compound of formula IIIa or IV by hydrogenolysis to form a compound of formula (I);

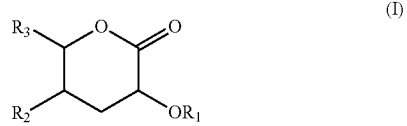

wherein $R_1$, $R_{1'}$, $R_{1''}$, $R_2$ and $R_3$ are as defined in respect of the first aspect of the invention and R is as defined for $R_1$.

In step a), a double elimination reaction may occur to arrive at a compound of formula (IIIa) or a single elimination can occur to arrive at a compound of formula (IIIb). Whether a single or double elimination occurs can be controlled by controlling the strength of the base. Use of a milder base will ensure that only one elimination occurs.

It should be appreciated that the optional step b) is carried out where in the desired compound of formula (I), $R_3$ is methyl. This step preferably comprises exposure of a compound of formula IIIa to excess base for a prolonged period in order to allow a third elimination to occur.

Thus, in one embodiment, there is provided a process for the preparation of a lactone compound of formula (I), wherein $R_3$ is —$CH_2OR_{1''}$ and $R_2$ is hydrogen, the process comprising the steps of:

a) reacting a tetra-O-substituted(R)-D-gluconolactone of formula II with a base to form a compound of formula IIIa; and
b) reducing the compound of formula IIIa by hydrogenolysis to form a compound of formula I wherein $R_3$ is —$CH_2OR_{1''}$ and $R_2$ is hydrogen.

In an alternative embodiment, there is provided a process for the preparation of a lactone compound of formula (I), wherein $R_3$ is methyl and $R_2$ is hydrogen, the process comprising the steps of:
a) reacting a tetra-O-substituted(R)-D-gluconolactone of formula II with a base to form a compound of formula IIIa;
b) further reacting the compound of formula IIIa with a base to form a compound of formula IV; and
c) reducing the compound of formula IV by hydrogenolysis to form a compound of formula (I) wherein $R_3$ is methyl and $R_2$ is hydrogen.

Preferably, step b) comprises exposure of the compound of formula IIIa to excess base for a prolonged period. Preferably, steps a) and b) are telescoped into a single reaction step, wherein the compound of formula IIIa is formed as an intermediate in situ, but is not isolated.

In a further alternative embodiment, there is provided a process for the preparation of a lactone compound of formula (I), wherein $R_3$ is —$CH_2OR_{1''}$ and $R_2$ is —$CH_2OR_{1'}$ the process comprising the steps of:
a) reacting a tetra-O-substituted(R)-D-gluconolactone of formula II with a mild base to form a compound of formula IIIb;
b) reducing the compound of formula IIIb by hydrogenolysis to form a compound of formula I wherein $R_3$ is —$CH_2OR_{1''}$ and $R_2$ is —$CH_2OR_{1''}$.

In a preferred embodiment, the elimination steps carried out to form compounds of formula IIIb and IV are carried out in the presence of a base with or without solvent. Preferably, the base is triethylamine or pyridine. Where solvent is present, it is preferably methylene chloride.

Preferably, hydrogenolysis is carried out in the presence of $H_2$ and a Pd/C catalyst and a solvent. The solvent is preferably ethyl acetate.

The process described above is straightforward and leads to high yields of lactone. This is advantageous over prior syntheses which often involved many steps, had very low overall yields and involved difficult and low yielding purification of the lactone. Also, previously functionalized polymers were not commonly made from renewable resources. The process requires just two reaction steps, both of which can lead to >90% yield. Moreover, purification of the lactone compound is straightforward. In addition, the D-gluconolactone starting material derives from a relatively inexpensive, renewable resource (glucose).

In a preferred embodiment, the tetra-O-substituted(R)-D-gluconolactone of formula II is derived from D-gluconolactone. Preferably, the process further comprises the step of preparing the tetra-O-substituted(R)-D-gluconolactone of formula II from gluconolactone by acetylation reaction of D-gluconolactone with a compound of formula R*C(O)OC(O)R* (e.g. acetic anhydride) wherein R* is alkyl, haloalkyl, aryl or heteroaryl, preferably alkyl or haloalkyl, more preferably alkyl. Preferably, the reaction of D-gluconolactone with a compound of formula R*C(O)OC(O)R* is telescoped with the elimination steps carried out to form compounds of formula IIIa, IIIb or IV into a single reaction step in which D-gluconolactone is reacted with a compound of formula R*C(O)OC(O)R* in the presence of base to produce a compound of formula III. For the purposes of this invention, telescoping of reaction steps is the practice of joining together consecutive reaction steps and avoiding isolation of the compounds produced by each reaction step. Advantageously, the telescoping of the acetylation and elimination into a single reaction step increases reaction yield considerably.

Therefore, in a preferred embodiment there is provided a process for the preparation of a lactone compound of formula (I) wherein $R_1$, $R_{1'}$ and $R_{1''}$ are acyl, the process comprising the steps of:

a) reacting D-gluconolactone with a compound of formula $R_1C(O)OC(O)R_1$ in the presence of base to form a compound of formula IIIa or IIIb, via a tetra-β-substituted (R)-D-gluconolactone in situ intermediate;

b) optionally further reacting the compound of formula IIIa with a base to form a compound of formula IV; and c) reducing the compound of formula IIIa or IV by hydrogenolysis to form a compound of formula (I).

In certain embodiments of the invention, the process requires a further step subsequent to production of the compound of formula IV to produce the desired lactone compound. In one embodiment, where the desired $R_1$ is benzyl, benzyl would be cleaved under the hydrogenation conditions so an additional substituent exchange step would be required. In addition, where $R_1$ is hydrogen a step of deprotection/removal of a substituent would be required to arrive at the lactone compound. This is feasible for substituents such as ester (e.g. t-Boc, Fmoc) or sulfonyl (tosyl).

In another preferred embodiment, the process further comprises the step of incorporating a peptide or drug molecule onto the functionalized lactone of formula (I). This can be achieved either by removal of an $R_1$ substituent (to yield $R_1$=H) and then reaction with the drug/peptide to attach it to the lactone or by reaction of the drug/peptide with one of the substituent groups present on the lactone compound.

In a fifth aspect, the present invention provides use of a polymer according to the first aspect of the invention for the production of a biomaterial (material derived from biological sources). Preferably, the polymer of the invention (or biomaterial derived therefrom) is for use as a packaging material or fibres, the polymer (or biomaterial) may also be of use for medical applications where degradable, functionalized materials are preferable such as degradable sutures, dressings, stent and implants or as a matrix for tissue engineering or as an excipient for drug delivery. The invention also provides use of the polymers of the invention (particularly copolymers) as an impact modifier for a conventional biodegradable packaging material.

In a sixth aspect, the present invention therefore provides a packaging material, a medical device such as a degradable suture, dressing, stent or implants, a matrix for tissue engineering or an excipient for drug delivery comprising a polymer according to the first aspect of the invention.

All preferred features of each of the aspect of the invention can be applied to the other aspects of the invention.

The invention may be put into practice in various ways and a number of specific embodiments will be described by way of example to illustrate the invention with reference to the accompanying figures, in which.

Figure 10:
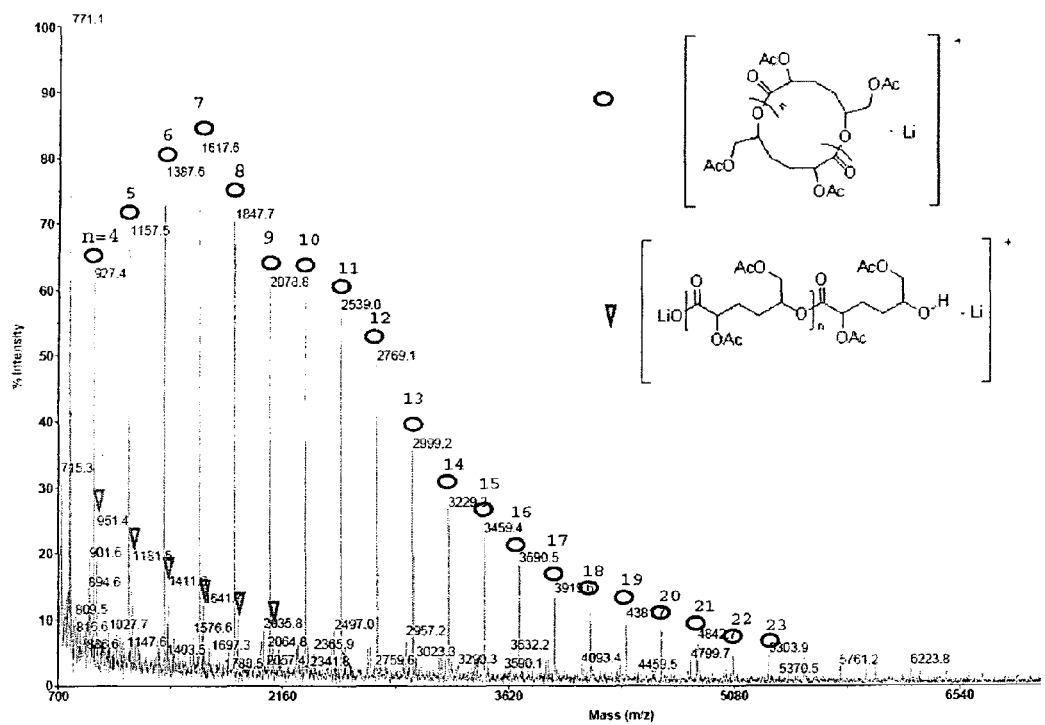

FIG. 10 shows a MALDI mass spectrum of poly(acetic acid-5-acetoxy-6-oxo-tetrahydro-pyran-2-yl-methyl ester) 4. The spectrum was run using a dithranol matrix and a LiCl additive. The spectrum was obtained for 1:100 loading of initiator:compound 3 at 60% conversion. Open circles represent the cyclic polymer and open triangles the linear chains end-capped with carboxylic acid and hydroxyl groups.

Figure 11:
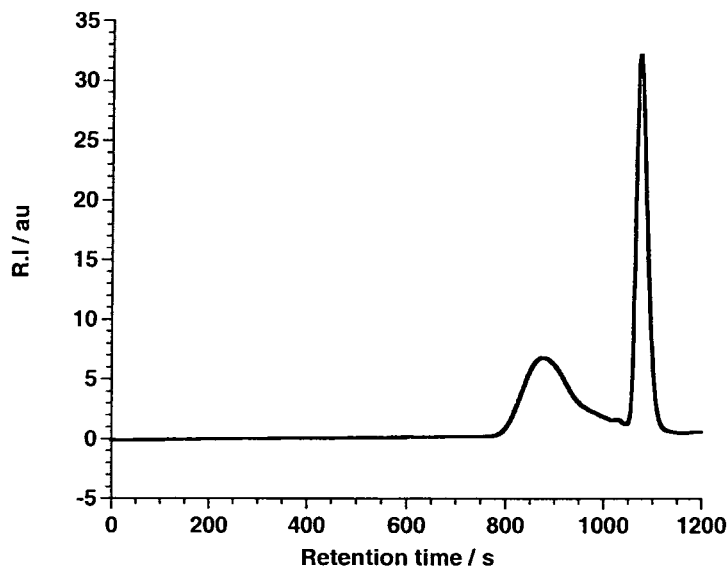

FIG. 11 shows an SEC trace for poly(acetic acid-5-acetoxy-6-oxo-tetrahydro-pyran-2-yl-methyl ester) 4. The trace shows the signal due to the polymer (retention time: 800-1000 s) and monomer (1100 s). Polymerization conditions: $[3]_0$=1 M, $[LZnOEt]_0$=0.01 M, CH$_2$Cl$_2$, 25° C. SEC conditions: CHCl$_3$, 1 mLmin$^{-1}$, two mixed B columns, polystyrene standards.

Figure 12:
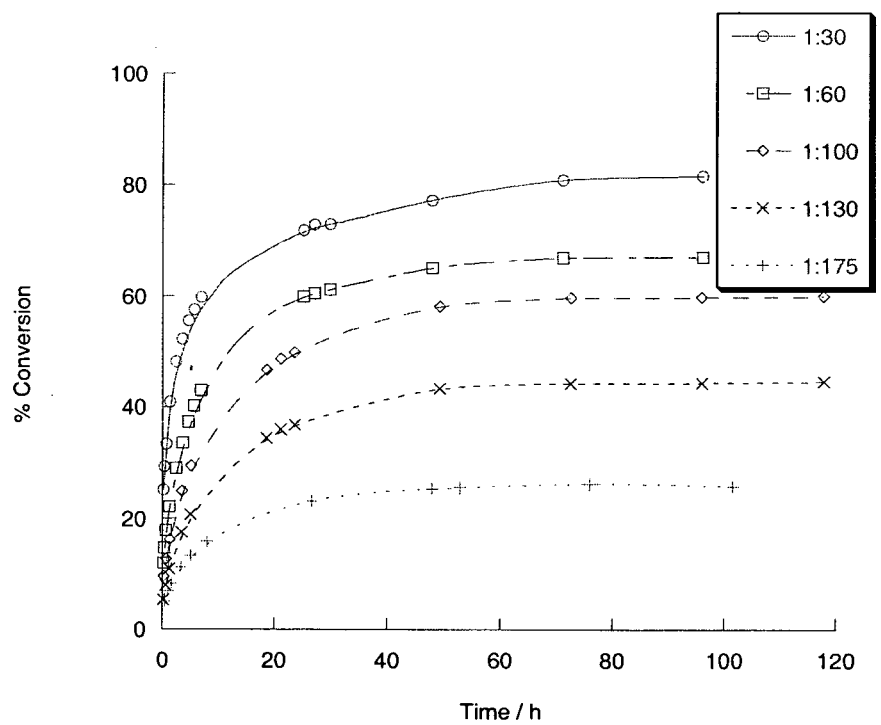

FIG. 12 show plots of % conversion of compound 3 to compound 4 versus time at various loadings of initiator.

Figure 13:
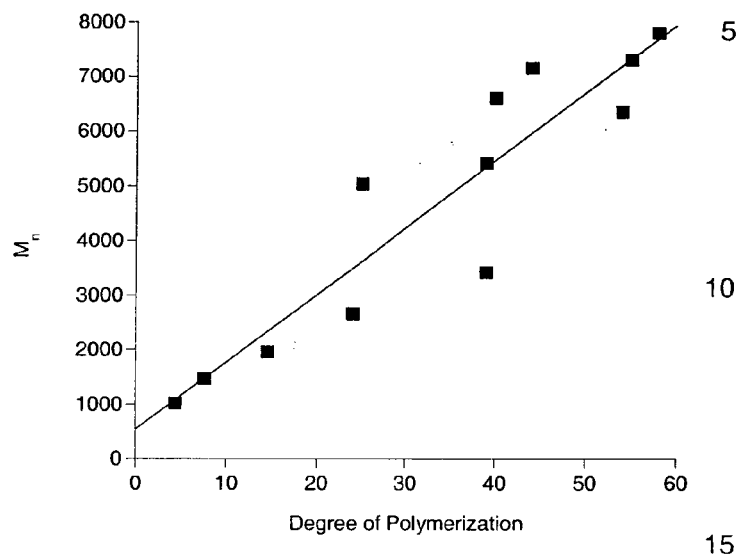

FIG. 13 shows a plot of degree of polymerization (DP) versus $M_n$.

Figure 14:
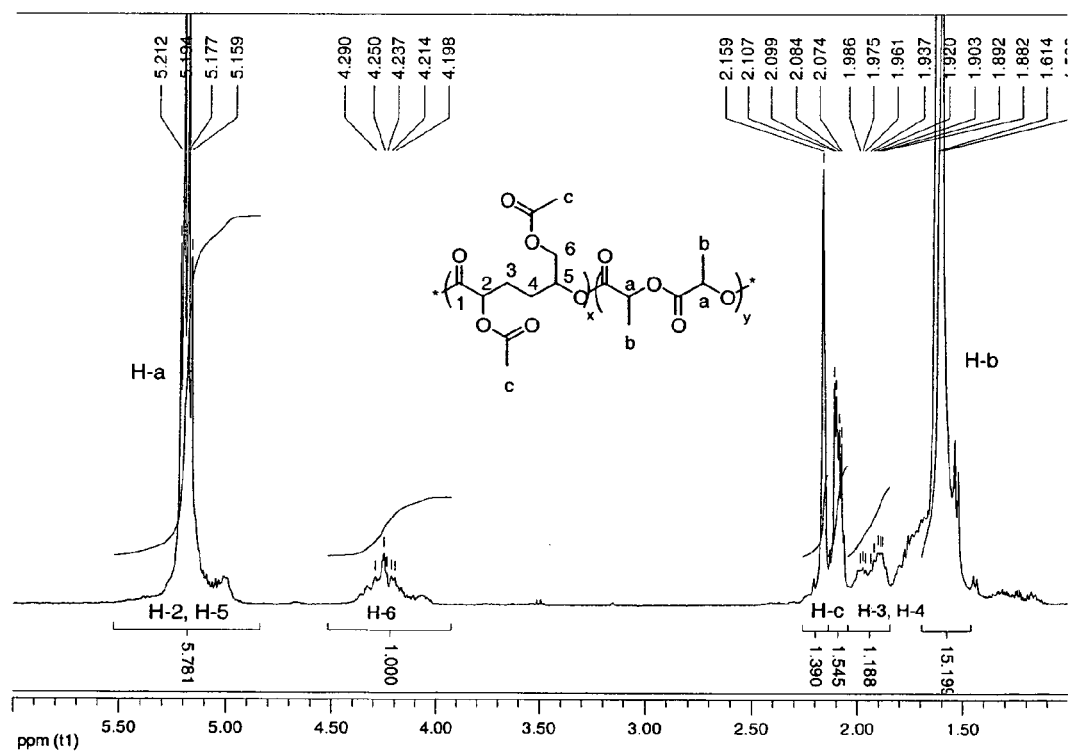

FIG. 14 shows a $^1$H NMR spectrum of a random copolymer (RP1) of compound 3 and S-lactide in CDCl$_3$ (Reaction conditions 25° C., THF).

The terms "comprises" is taken to mean "includes among other things" and should not be construed as "consist only of".

The term "alkyl" as used herein means an alkyl group that is a straight or branched chain, preferably having from 1 to 6 carbon atoms. Specifically, examples of a "$C_{1-6}$ alkyl" include but are not limited to methyl, ethyl, n-propyl, iso-propyl, n-butyl, iso-butyl, sec-butyl, tert-butyl, n-pentyl, 1,1-dimethylpropyl, 1,2-dimethylpropyl, 2,2-dimethylpropyl, 1-ethylpropyl, n-hexyl, 1-ethyl-2-methylpropyl, 1,1,2-trimethylpropyl, 1-ethylbutyl, 1-methylbutyl, 2-methylbutyl, 1,1-dimethylbutyl, 1,2-dimethylbutyl, 2,2-dimethylbutyl, 1,3-dimethylbutyl, 2,3-dimethylbutyl, 2-ethylbutyl, 2-methylpentyl, 3-methylpentyl and the like.

The term "haloalkyl" as used herein means an alkyl group as described above substituted with 1-3 halogen atom(s). Specifically, examples of a "$C_{1-6}$ haloalkyl group" include but are not limited to fluoromethyl, difluoromethyl, trifluoromethyl, fluoroethyl, difluoroethyl, trifluoroethyl, chloromethyl, bromomethyl, iodomethyl and the like.

The term "halogen atom" as used herein means a fluorine atom, a chlorine atom, a bromine atom, an iodine atom and the like, preferably a fluorine atom or a chlorine atom, and more preferably a fluorine atom.

The term "alkoxy" used herein means an oxy group that is bonded to an "alkyl" as defined above. Specifically, examples of "$C_{1-6}$ alkoxy group" include but are not limited to methoxy, ethoxy, n-propoxy, iso-propoxy, n-butoxy, iso-butoxy, sec-butoxy, tert-butoxy, n-pentyloxy, iso-pentyloxy, sec-pentyloxy, n-hexyloxy, iso-hexyloxy, 1,1-dimethylpropoxy, 1,2-dimethylpropoxy, 2,2-dimethylpropoxy, 2-methylbutoxy, 1-ethyl-2-methylpropoxy, 1,1,2-trimethylpropoxy, 1,1-dimethylbutoxy, 1,2-dimethylbutoxy, 2,2-dimethylbutoxy, 2,3- dimethylbutoxy, 1,3-dimethylbutoxy, 2-ethylbutoxy, 2-methylpentyloxy, 3-methylpentyloxy and the like.

The term "alkylamino" as used herein means an amino group which is substituted with an alkyl group as described above. The term "dialkylamino" as used herein means an amino group which is substituted with two alkyl groups as described above.

The term "aryl" as used herein means an aryl group preferably constituted by 6 to 14 carbon atoms and includes condensed ring groups such as monocyclic ring group, a bicyclic ring group, a tricyclic ring group and the like. Specifically, examples of an aryl include phenyl, indenyl, naphthyl and the like. Preferably, aryl is phenyl.

The term "heteroaryl" as used herein means a monocyclic, bicyclic or tricyclic aromatic ring system in which one or more ring atom is a heteroatom selected from O, S or N. Preferably, a heteroaryl is a 5 to 7, preferably 5 to 6 membered monocyclic ring, for example pyrrolyl, pyridyl, pyridazinyl, pyrimidinyl, pyrazinyl, triazolyl, tetrazolyl, pyrazolyl, imidazolyl, thienyl; furyl, pyranyl, thiazolyl, isothiazolyl, isoxazolyl, furazanyl, oxazolyl, oxadiazolyl, pyrazolooxazolyl, imidazothiazolyl, furopyrrolyl or pyridooxazinyl and the like.

The terms "alkylaryl" and "alkylheteroaryl" as used herein mean an alkyl group substituted with an aryl or heteroaryl group, all as defined above.

The term "acyl" as used herein means a group having the structure —C(O)R*, wherein R* is an alkyl, haloalkyl, aryl or heteroaryl as defined above. Preferably, R* is alkyl, haloalkyl, aryl, heteroaryl, alkylaryl, alkylheteroaryl. More preferably, R* is alkyl or haloalkyl. Most preferably, R* is alkyl.

The term "ester" as used herein means a group having the structure —C(O)OR*, wherein R* is as defined above. In certain embodiments, ester may be $^t$BuOCO or Fmoc.

The term "sulfonyl" as used herein means a group having the structure —SO$_2$R*, wherein R* is as defined above.

It should be appreciated that each of the aryl, alkyl and heteroaryl groups described herein may be unsubstituted or substituted with one or more substituents independently selected from C$_{1-6}$ alkyl, nitro, amino, alkylamino, dialkylamino and halogen.

A carbohydrate lactone of the invention can be prepared in simple, high yield steps from commercially available D-gluconolactone as represented by Scheme 1. In step a), D-gluconolactone 1 is converted to 2 in quantitative yield by reaction with acetic anhydride and base. Compound 2 is then reduced by hydrogenolysis, again in quantitative (>95%) yield, to produced lactone 3. This lactone can then be polymerized in a ring opening polymerization reaction. This is shown in Scheme 1.

Scheme 1: Synthesis of 3 and its ring-opening polymerization to 4.

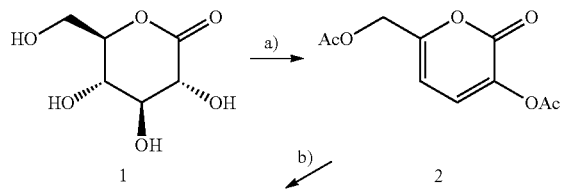

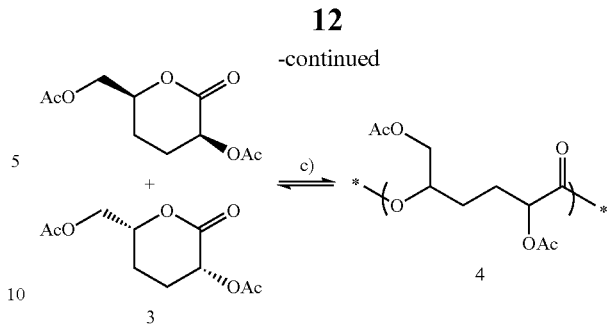

Reagents and conditions: a) Ac$_2$O, pyridine, 80° C., 1 h, 95%. b) H$_2$ (50 bar), Pd/C, EtOAc, 75° C., 24 h, 95%. c) LZnOEt, CDCl$_3$ (1M solution of 3), 25° C., 48 h.

The invention will now be illustrated by reference to the following non-limiting examples.

Materials

The zinc ethoxide complex (LZnOEt) was prepared and used according to the literature (Williams, C. K. et al, J. Am. Chem. Soc., 2003, 123, 11350). Diethyl ether was dried by distillation from sodium, ethyl acetate and d-chloroform were dried by distillation from calcium hydride. All other reagents and chemicals were purchased from Aldrich Chemical Co. and used as received. All manipulations were carried out under a dry nitrogen atmosphere either on a Schlenk line or in an MBraun nitrogen filled glove box.

Measurements

NMR spectra were performed on Bruker AV400 and AV500 instruments. CDCl$_3$ was used as the NMR solvent and reference compound. Elemental analyses were conducted by Mr Stephen Boyer, London Metropolitan University, Holloway Rd, London. The SEC measurements were performed on a Polymer labs SEC 60 instrument with two Polymer labs mixed D columns and THF at a flow rate of 1 mLmin$^{-1}$ as the eluent. Narrow molecular weight polystyrene standards were used to calibrate the instrument.

EXAMPLE 1

Preparation of Acetic acid 5-acetoxy-6-oxo-tetrahydro-pyran-2-ylmethylester (3)

Conversion of D-gluconolactone (1) to 3-Acetoxy-6-acetoxymethyl-pyran-2-one (2) in quantitative yield by reaction with acetic anhydride and pyridine D-Glucono-1,5-lactone 1 (6.00 g, 33.7 mmol) was stirred with acetic anhydride (20 mL) and anhydrous pyridine (20 mL) at 80° C. for 1 hour. The mixture was poured onto crushed ice (400 mL) and extracted with CHCl$_3$ (2×300 mL). The combined organic layers was washed with ice-cold water (2×200 mL), dried (MgSO$_4$) and filtered. The solution was treated with activated carbon, filtered and concentrated. The product was dried in vacuo and yielded a yellow syrup (7.30 g, 32.3 mmol, 96%). $^1$14 NMR (CDCl$_3$, 400 MHz) δ: 7.10 (1H, d, $^3J_{H-H}$=7.09 Hz, H-3), 6.28 (1H, dd, $^3J_{H-H}$=7.16 Hz, H-4), 4.86 (2H, s, H-6, H-6'), 2.33, 2.15 (2×3H, 2×s, COCH$_3$) ppm.

Reduction of 3-Acetoxy-6-acetoxymethyl-pyran-2-one (2) to produce acetic acid 5-acetoxy-6-oxo-tetrahydro-pyran-2-ylmethyl ester (3)

3-Acetoxy-6-acetoxymethyl-pyran-2-one 2 (4.80 g, 21.2 mmol) was dissolved in ethyl acetate (50 mL) and added to a Parr reactor, followed by Pd/C (0.20 g, 1.06 mmol). The mixture was stirred under hydrogen (5×10⁶ Pa) and heated to 75° C. for 1 day. The product was filtered through celite and concentrated to yield a colourless syrup (4.83 g, 21.0 mmol, 99%). The crude product was purified by repeated recrystallization from diethyl ether and dried in vacuo to yield white crystals (2.44 g, 10.6 mmol, 50%).

M. pt. 93.5-94.5° C. Anal. Calcd for $C_{10}H_{14}O_6$: C, 52.17%; H, 6.13%. Found: C, 52.11%; H, 6.17%. $^1$H NMR (400 MHz, CDCl$_3$) δ: 5.44 (1H, dd, $^3J_{H-H}$=17.08 Hz, $^3J_{H-H}$=8.55 Hz, H-2), 4.65 (1H, m, H-5), 4.26 (1 H, dd, $^2J_{H-H}$=12.13 Hz, $^3J_{H-H}$=3.54 Hz, H-6), 4.18 (1 H, dd, $^2J_{H-H}$=12.16, $^3J_{H-H}$=6.32 Hz, H-6'), 2.36 (1H, m, H-3), 2.19 (3H, s, COCH$_3$), 2.12 (3H, s, COCH$_3$), 2.07-1.88 (3H, m, H-3', H-4, H-4') ppm. $^{13}$C{$^1$H} NMR (125 MHz, CDCl$_3$) δ: 170.6, 169.8, 168.6 (2×COCH$_3$, C-1), 74.9 (C-5), 65.9 (C-2), 64.9 (C-6), 22.7, 22.4 (C-3, C-4), 20.7 (2×COCH$_3$) ppm. m/z (CI-ammonia gas): 248 [M+NH$_4^+$]. [α]$_D$=0° (CHCl$_3$, 10 mg/mL). IR (paraffin) ν: 2959, 1766, 1732, 1457, 1377, 1348, 1099, 1059, 1036, 976 cm$^{-1}$.

Figure 1:
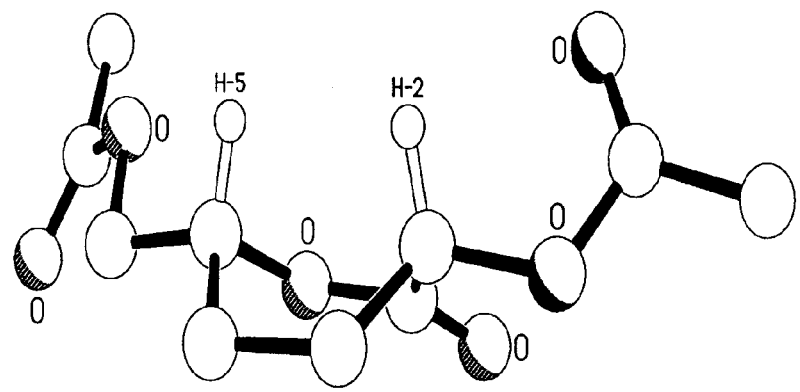
FIG. 1 shows the X-ray crystal structure of a lactone compounds of the invention a) (acetic acid 5-acetoxy-6-oxo-tetrahydro-pyran-2-ylmethyl ester 3); and b) 6-methyl-2-oxo-tetrahydro-2H-pyran-3-yl acetate.
Figure 1:
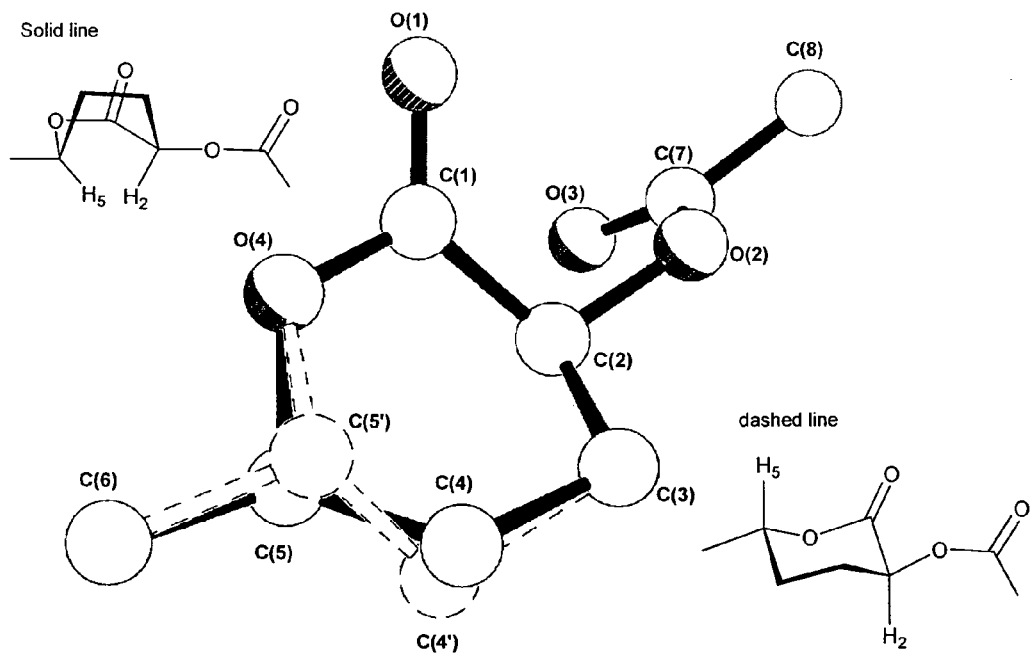
Figure 2A:
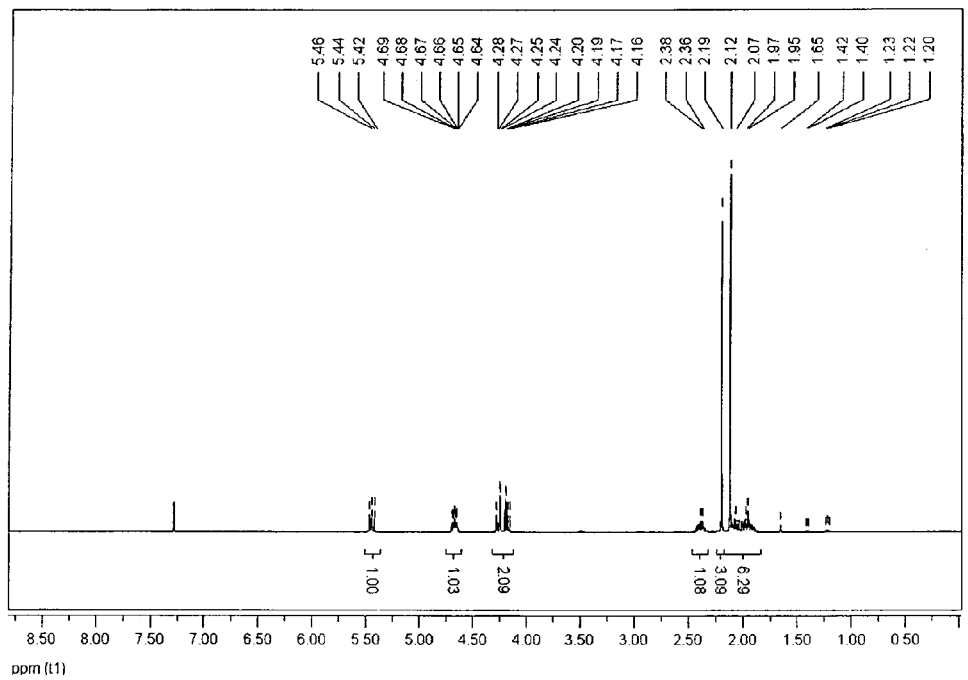
FIG. 2 shows an $^1$H NMR spectrum of acetic acid 5-acetoxy-6-oxo-tetrahydro-pyran-2-ylmethyl ester 3.
Figure 2B:
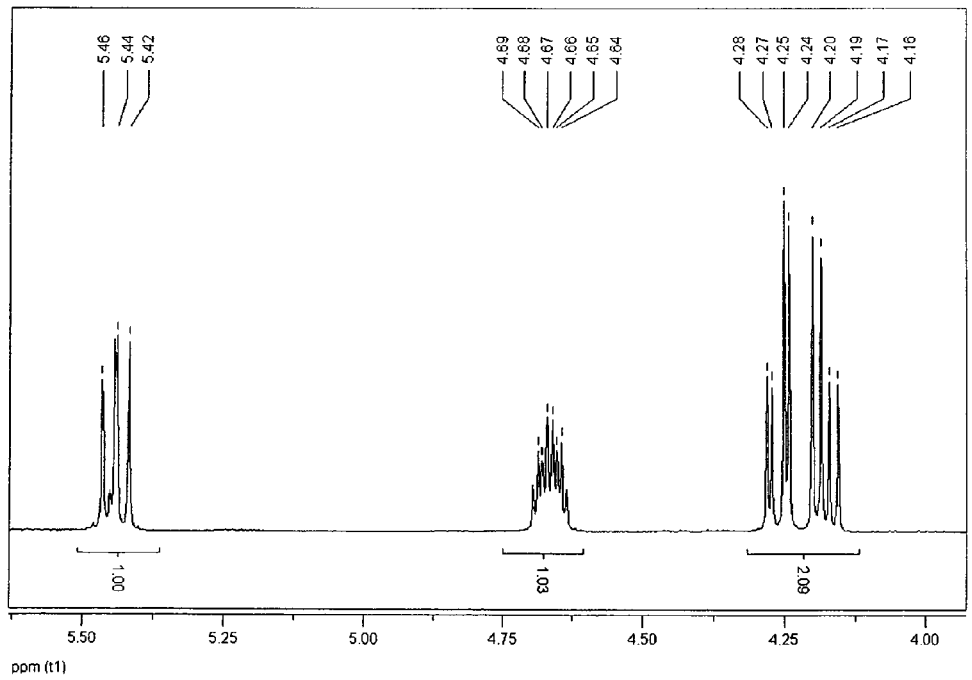
Figure 2C:
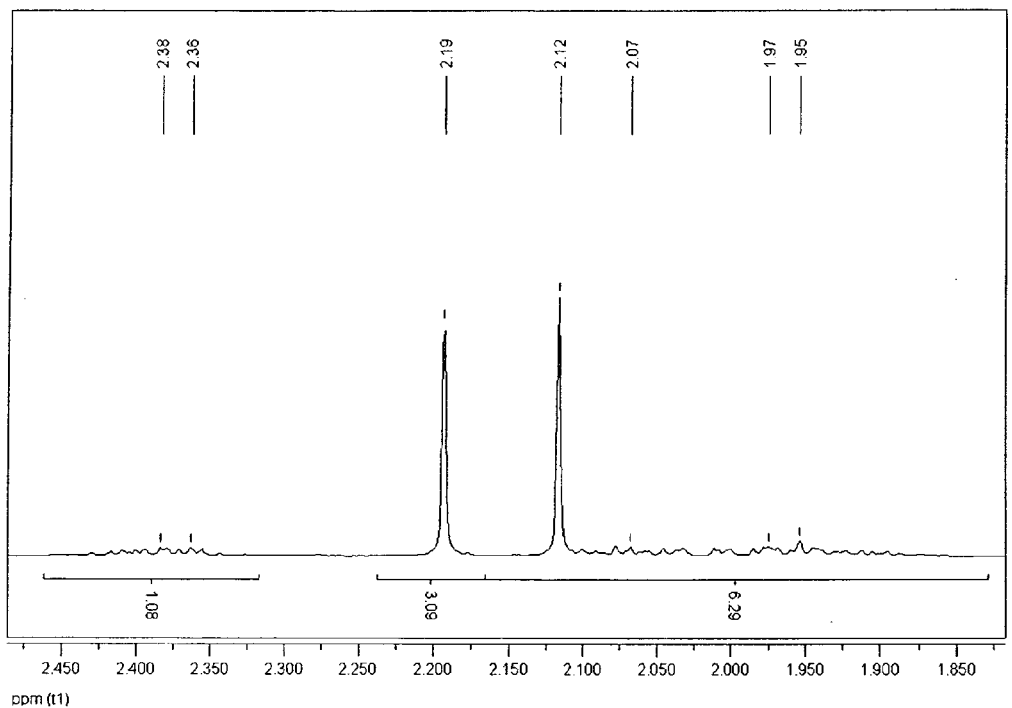
Figure 3:
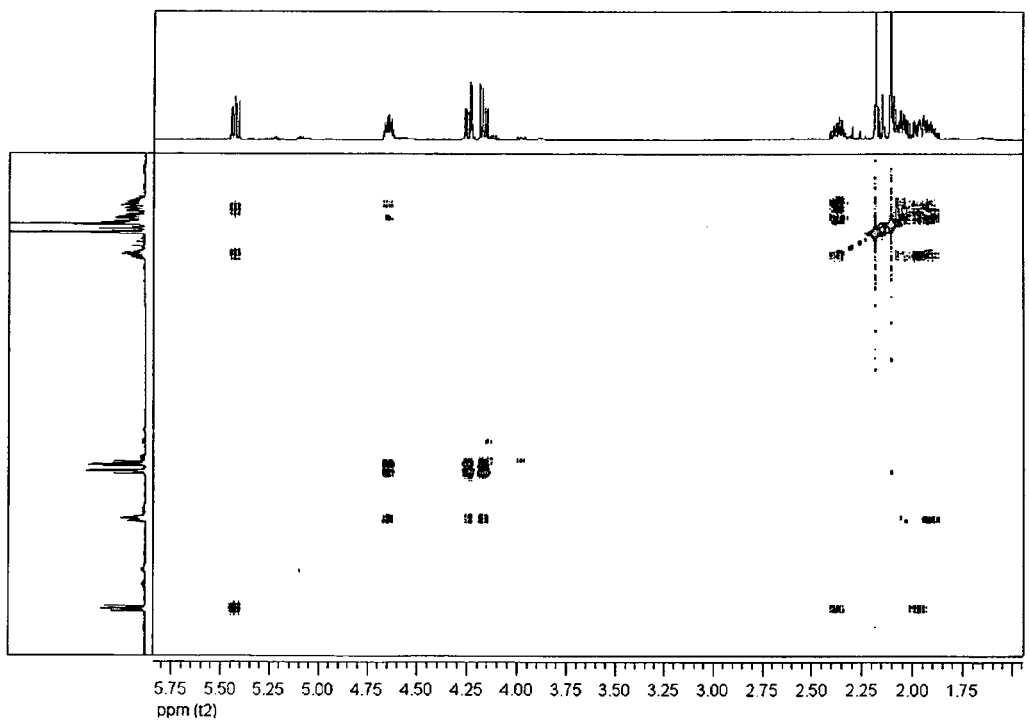
FIG. 3 shows a COSY spectrum of acetic acid 5-acetoxy-6-oxo-tetrahydro-pyran-2-ylmethyl ester 3.
Figure 4:
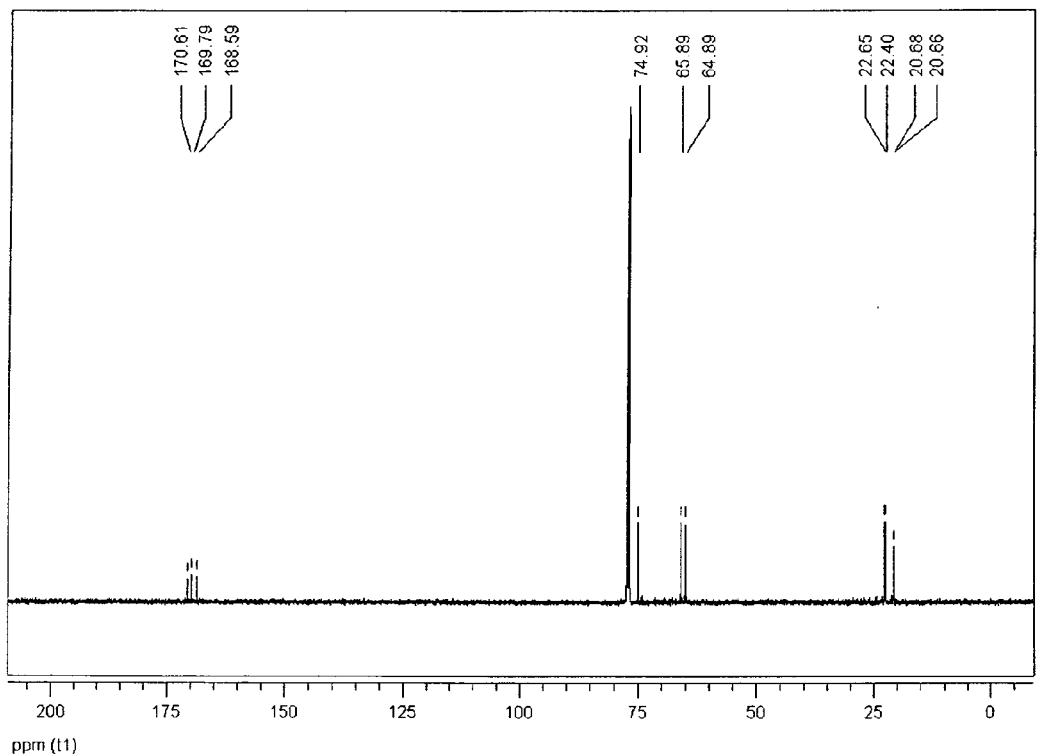
FIG. 4 shows a $^{13}C\{^1H\}$ NMR spectrum of acetic acid 5-acetoxy-6-oxo-tetrahydro-pyran-2-ylmethyl ester 3 in CDCl$_3$.
Figure 5:
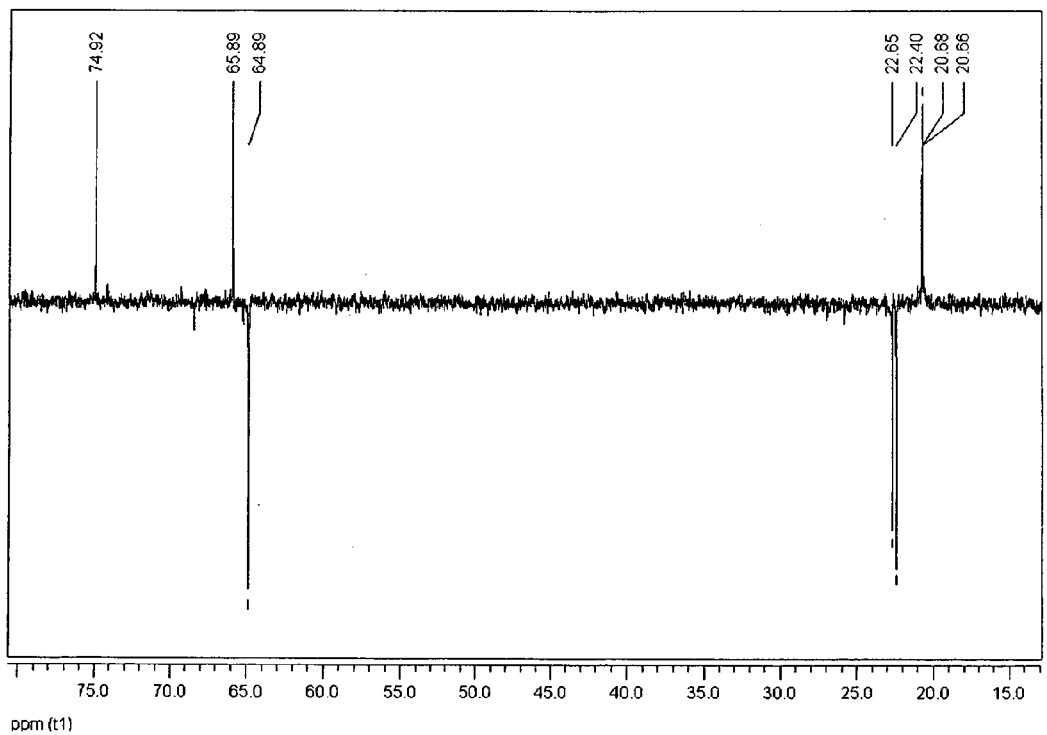
FIG. 5 shows a DEPT-135 spectrum of acetic acid 5-acetoxy-6-oxo-tetrahydro-pyran-2-ylmethyl ester 3.
Figure 6:
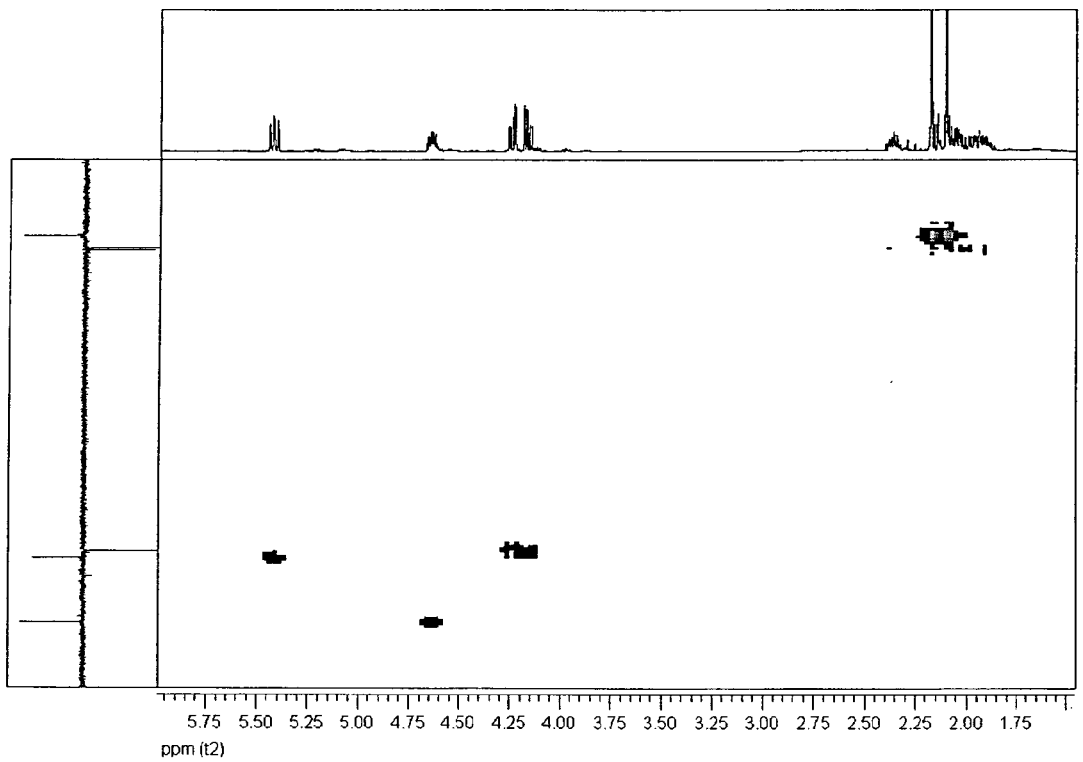
FIG. 6 shows a HMQC spectrum of acetic acid 5-acetoxy-6-oxo-tetrahydro-pyran-2-ylmethyl ester 3.
Figure 7:
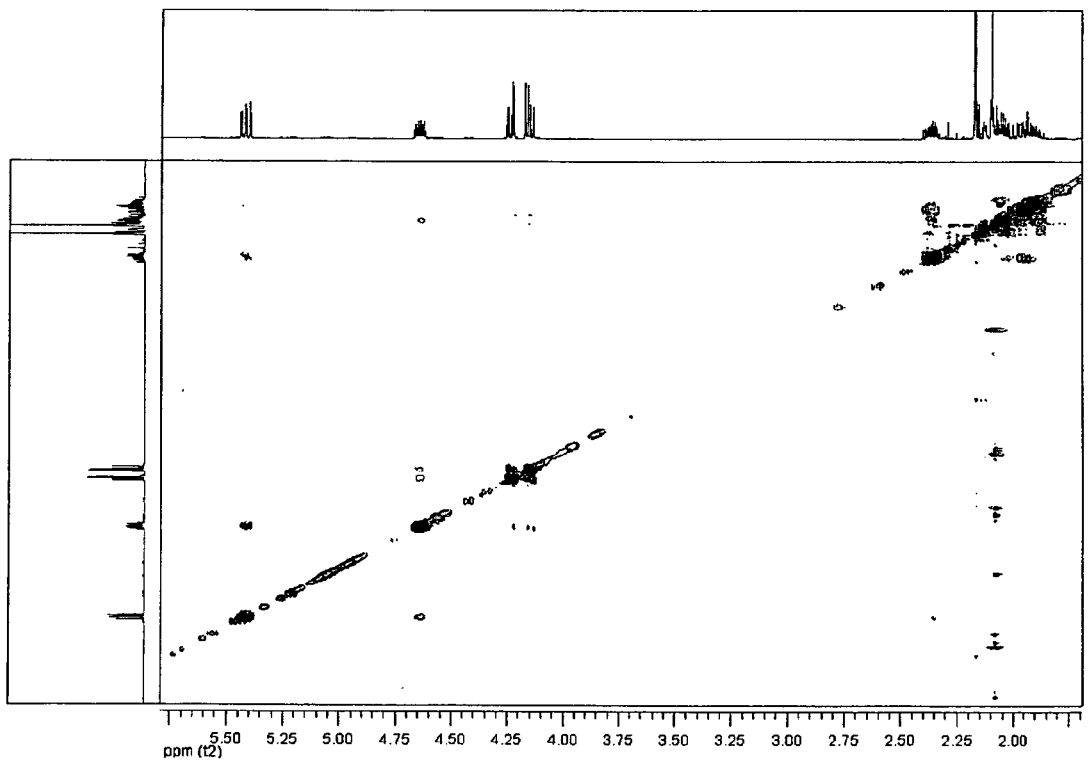
FIG. 7 shows a NOESY spectrum of acetic acid 5-acetoxy-6-oxo-tetrahydro-pyran-2-ylmethyl ester 3.

The hydrogenolysis reaction set out above was diastereoselective, yielding only the syn enantiomers of compound 3. Compound 3 was isolated as a racemic mixture, established by a lack of specific rotation and by X-ray crystallography. The X-ray crystal structure of 3 shows the carbohydrate ring in a boat conformation (see FIG. 1). This boat conformation is maintained in solution, as confirmed by the $^3J_{HH}$ values and the strong correlation in the NOESY NMR spectrum between H-2 and H-5 (FIGS. 2, 3 and 7).

EXAMPLE 2

Polymerization of Acetic acid 5-acetoxy-6-oxo-tetrahydro-pyran-2-ylmethyl ester (3) to produce poly (acetic acid-5-acetoxy-6-oxo-tetrahydro-pyran-2-ylmethyl ester) (4)

Monomer 3 (0.138 g, 0.6 mmol, 1 eq) was dissolved in CDCl$_3$ (0.045 mL) and added into a Young's tap NMR tube, followed by the initiator stock solution (0.015 mL of a 0.04 M solution of initiator LZnOEt, having the structure set out below, in CDCl$_3$, 0.01 eq).

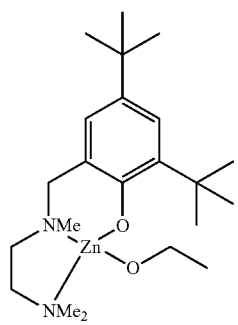

The polymerization was monitored by $^1$H NMR every hour. By integration of the H-2 signals, at 5.45 ppm for 3 and 5.00 ppm for 4, and the H-5 signals, at 4.65 ppm for 3 and 5.14 ppm for 4, the percentage conversion was determined. After the polymerization reached equilibrium, 4 was purified by repeated precipitation in diethyl ether (3×30 mL) and dried in vacuo.

$^1$H NMR (400 MHz, CDCl$_3$) δ: 5.14 (1H, bs, H-5), 5.00 (1H, H-2), 4.28-4.05 (2H, H-6), 2.15 (3H, s, COCH$_3$), 2.09 (3H, s, COCH$_3$), 1.89 (2H, H-3), 1.72 (2H, H-4) ppm. $^{13}$C{$^1$H} NMR (125 MHz, CDCl$_3$) δ 171.2-169.4 (C=O), 71.9-71.4 (C-2), 70.2-70.1 (C-5), 65.6-64.4 (C-6), 26.6-26.2 (C-3, C-4), 20.9-20.5 (3×COCH$_3$) ppm.

The ring opening polymerization described above was initiated with a single site zinc initiator (LZnOEt). The polymerizations were performed under mild conditions, at 1 M concentration of 3 in CDCl$_3$ at 25° C.

Figure 8:
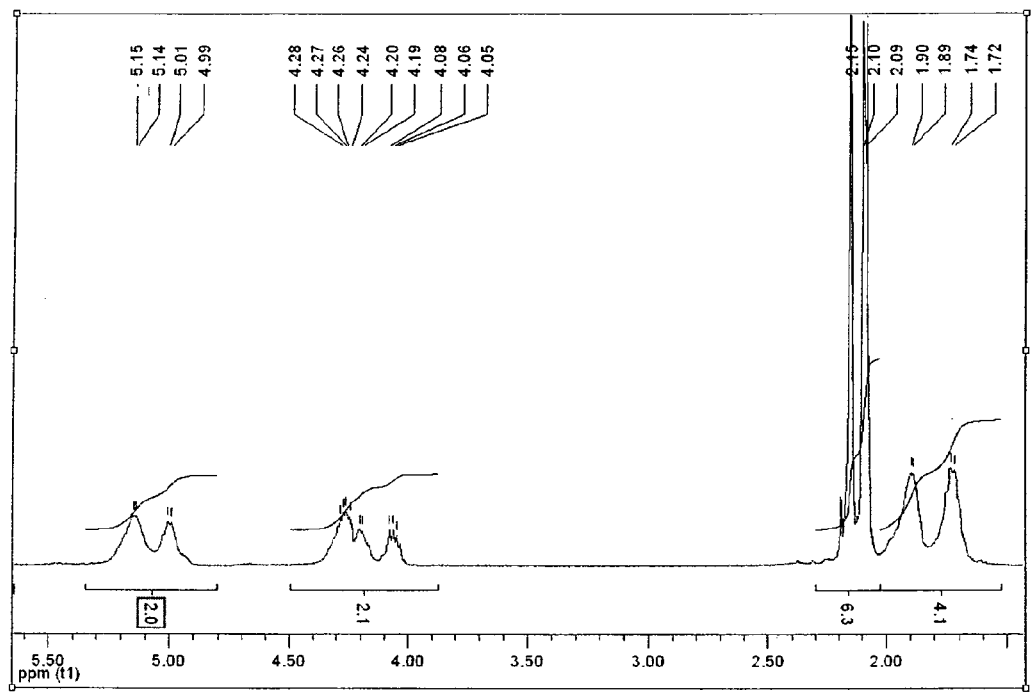
FIG. 8 shows an NMR spectrum of poly(acetic acid-5-acetoxy-6-oxo-tetrahydro-pyran-2-yl-methyl ester) 4.
Figure 9:
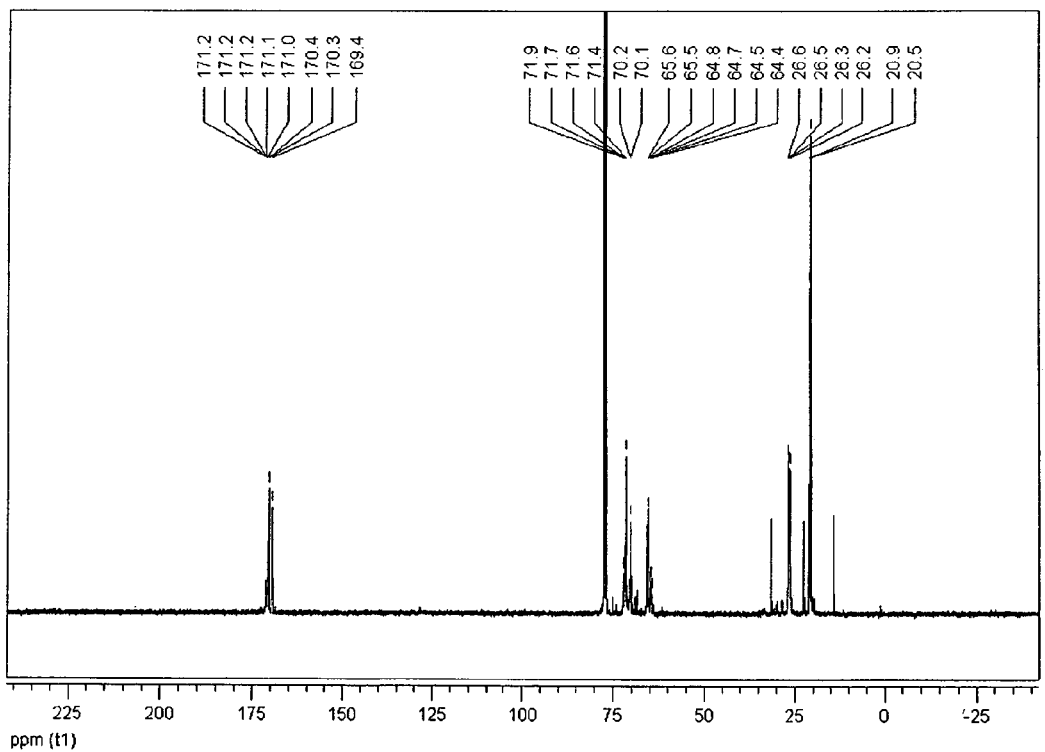
FIG. 9 shows an $^{13}C\{^1H\}$ NMR spectrum of poly(acetic acid-5-acetoxy-6-oxo-tetrahydro-pyran-2-yl-methyl ester) 4.

The polymerizations were monitored by $^1$H NMR spectroscopy, where shifting and broadening of resonances was observed (FIGS. 2 to 7 for compound 3 and FIGS. 8 and 9 for polymer 4). The $^{13}$C{$^1$H} NMR shows multiple, overlapping signals for C-1 indicating an atactic polymer is formed. This is in line with the preparation of atactic polylactide from rac-lactide using the same initiator. The percentage conversion was determined by integrating the resonances assigned to H-2 and H-5. However, the polymer 4 does not show any end-group resonances in the $^1$H NMR spectrum. The MALDI mass spectrum shows that the major product is a cyclic polymer (FIG. 10). There is also a minor proportion of a linear polyester with a carboxylic acid and hydroxyl end groups. The acetate side groups do not undergo transesterification reactions unless the polymerization is left at equilibrium for a prolonged period. The SEC measurements (FIG. 11) confirm the polymer formation, but give M$_n$, lower than expected (Table 1) in accordance with the formation of cyclic polymer.

TABLE 1

Measurements for the polymerization of compound 3.

| (3):Initiator[a] | Time/h | Equilibrium conversion[b]/% (DP) | M$_n$(SEC)[c] (PDI) | M$_n$(calc.)[d] |
|---|---|---|---|---|
| 30:1 | 71 | 80 (25) | 5044 (1.34) | 5750 |
| 50:1 | 48 | 78 (39) | 5422 (1.48) | 8970 |
| 65:1 | 48 | 66 (40) | 6608 (1.25) | 9200 |
| 100:1 | 48 | 58 (58) | 7804 (1.23) | 13,340 |
| 130:1 | 48 | 44 (55) | 7312 (1.29) | 12,650 |

[a]polymerization conditions were LZnOEt (1 eq) CDCl$_3$, 25° C., [3]$_0$ = 1M;
[b]conversion determined from $^1$H NMR spectrum by normalized integration of the signals due to H-2 and H-5 for 3 and 4;
[c]determined by SEC in THF vs. polystyrene standards;
[d]calculated from the degree of polymerization derived from $^1$H NMR: M$_n$(calc.) = [(230 × DP)].

The polymerizations are equilibrium reactions (FIG. 12) and Table 1 shows that the conversion and degree of polymerization (DP) of compound 3 vary with the loading of initiator LZnOEt. At high initiator loadings the degree of polymerization increases to approximately 60, but with a further decrease in initiator concentration, the DP remains constant.

The polymerizations are quite slow, taking 2 days to reach equilibrium. The same initiator takes minutes to polymerize lactide under similar conditions. It is possible that the slow rate of polymerization vs. intramolecular transesterification favours cyclic formation. In any case, it is remarkable that compound 3 polymerizes at all, as ring-opening polymerization is usually disfavoured for valerolactone derivatives with more than one substituent (Carruthers, W. H. et al., J. Am. Chem. Soc. 1932, 761-772). Without wishing to be bound by theory, it is proposed that the unusual boat conformation of compound 3 and/or the propensity of compound 3 to form cyclic polymers contribute to enabling polymerization. The ring-opening polymerization is well controlled, as exemplified by the linear increase in M$_n$, with DP (FIG. 13) and the narrow polydispersity indices (PDIs). Controlled polymerization is important for applications of polymers because it enables accurate prediction of the Mn and properties of the polymer from the stoichiometry of the polymerization reaction.

The polyester, 4, is significantly more hydrophilic than polylactide. It swells when water is added to it and has a water contact angle 4 of approximately 33°. It is an amorphous elastomer, the DSC shows no melting temperature and a glass transition temperature of 17° C. (FIG. 13). However, the polymer is thermally stable, TGA shows that degradation begins at 250° C.

EXAMPLE 3

Preparation and Ring opening polymerisation of 6-Methyl-2-oxo-tetrahydro-2H-pyran-3-yl acetate (4.25)

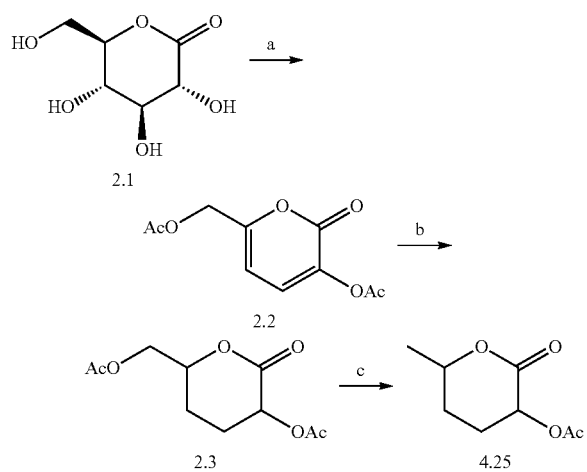

(a) Ac₂O, pyridine, 80° C., 1 h, 90%; (b) Pd/C (5%), H₂, 99%; (c) Pd/C (5%), H₂, Et₃N, 70%.

3-Acetoxy-6-acetoxymethyl-pyran-2-one (2.2)

D-Glucono-1,5-lactone (6.00 g, 33.7 mmol) was stirred with acetic anhydride (20 mL) and anhydrous pyridine (20 mL), at 80° C. for 1 hour. The mixture was poured onto crushed ice (400 mL) and extracted with CHCl₃ (2×300 mL). The combined organic layers were washed with ice-cold water (2×200 mL), dried (MgSO₄) and filtered. The solution was treated with activated carbon, filtered and concentrated. The product was dried under vacuum and yielded a dark yellow syrup (7.3 g, 32.3 mmol, 96%). $^1$H NMR (CDCl₃, 400 MHz) δ 7.10 (1H, d, $^3J_{H-H}$=7.09 Hz, H-3), 6.28 (1H, dd, $^3J_{H-H}$=7.16 Hz, H-4), 4.86 (2H, s, H-6, H-6'), 2.33, 2.15 (2×3H, COCH₃) ppm. m/z (CI-ammonia gas): 244 [M+NH₄⁺].

Acetic acid 5-acetoxy-6-oxo-tetrahydro-pyran-2-ylmethyl ester (2.3)

3-Acetoxy-6-acetoxymethyl-pyran-2-one (2.2) (4.80 g, 21.2 mmol) was dissolved in ethyl acetate (50 mL) and added to the Parr reactor, followed by Pd/C (5%, 0.2 g). The mixture was stirred under hydrogen (5×10⁶ Pa) and heated to 75° C. for 4 hours. The product was filtered through celite and the solvent removed under vacuum. A colourless syrup was obtained (4.83 g, 21.0 mmol, 99%). $^1$H NMR (400 MHz, CDCl₃) δ 5.45 (1H, dd, $^3J_{H-H}$=17.08 Hz, $^3J_{H-H}$=8.55 Hz, H-2), 4.65 (1H, m, H-5), 4.26 (1 H, dd, $^2J_{H-H}$=12.13 Hz, $^3J_{H-H}$=3.54 Hz, H-6), 4.18 (1 H, dd, $^2J_{H-H}$=12.16, $^3J_{H-H}$=6.32 Hz, H-6'), 2.36 (1H, m, H-3), 2.19 (3H, s, COCH₃), 2.11 (3H, s, COCH₃), 2.07-1.88 (3H, m, H-3', H-4, H-4') ppm. $^{13}$C{$^1$H} NMR (125 MHz, CDCl₃) δ 170.6, 169.8, 168.6 (2×COCH₃, C-1), 74.9 (C-5), 65.9 (C-2), 64.9 (C-6), 22.7, 22.4 (C-3, C-4), 20.7 (2×COCH₃) ppm. CI (NH₄⁺): 248 (100%), 306 (30%), 478 (20%). m/z (CI-ammonia gas): 248 [M+NH₄⁺]. [α]$_D$=0° (CHCl₃, 10 mg/mL). Anal. Calcd for C₁₀H₁₄O₆: C, 52.17; H, 6.13. Found: C, 52.11; H, 6.17.

6-Methyl-2-oxo-tetrahydro-2H-pyran-3-yl acetate (4.25)

Acetic acid 5-acetoxy-6-oxo-tetrahydro-pyran-2-ylmethyl ester (2.3) (2.30 g, 10.0 mmol) was dissolved in ethyl acetate (50 mL) and added to the Parr reactor, followed by Pd/C (5%, 0.2 g) and triethylamine (4.3 mL, 30.0 mmol). The mixture was stirred under hydrogen (5×10⁶ Pa) and heated at 50° C. for 1 day. The product was filtered through celite and the solvent removed under vacuum. The crude product was dissolved in CH₂Cl₂ (200 mL) and washed with water (3×200 mL). The solvent was removed and the resulting product dried under vacuum. The resulting syrup was sublimed under vacuum, at 50° C., affording white crystals (1.20 g, 7.0 mmol, 70%). $^1$H NMR (400 MHz, CDCl₃) δ 5.46 (1H, dd, $^3J_{H-H}$=10.56 Hz, $^3J_{H-H}$=8.87 Hz, H-2), 4.60 (1H, m, H-5), 2.36 (1H, m, H-3), 2.20 (3H, s, COCH₃), 2.12-2.00 (1H, m, H-4), 2.00-1.88 (1H, m, H-3'), 1.88-1.75 (1H, m, H-4'), 1.42 (3H, d, $^3J_{H-H}$=6.22 Hz, H-6) ppm. $^{13}$C {$^1$H} NMR (125 MHz, CDCl₃) δ 169.9, 169.6 (COCH₃, C-1), 74.2 (C-5), 66.0 (C-2), 27.8 (C-4), 23.0 (C-3), 21.0 (C-6), 20.8 (COCH₃) ppm. m/z (CI-ammonia gas): 190 [M₊NH₄⁺]. Anal. Calcd for C₈H₁₂O₄: C, 55.81; H, 7.02. Found: C, 55.81; H, 7.05.

Ring-Opening Polymerization (ROP) of Monomer 4.25:

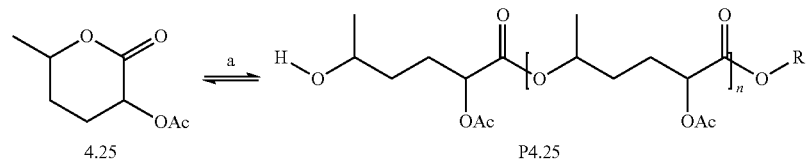

(a) ROP initiator, e.g. LZnOEt, RT, CDCl₃ or Sn(OBu)₂, toluene, 80° C.

The ROP of monomer 4.25 using LZnOEt as the initiator in CDCl₃ at RT:

| run | 4.25: initiator | [monomer]₀ | [initiator] | Final Conversion | M$_n$ (PDI) |
|---|---|---|---|---|---|
| 1 | 20:1 | 1M | 0.05M | 4.8% | 794 (1.09) |
| 2 | 50:1 | 1M | 0.02M | 2.3% | 786 (1.08) |

The ROP of 4.25 was investigated under various conditions Using the zinc initiatior yielded oligomeric products. Similar results were obtained when Sn(OBu)$_2$ was used as the initiator, although the reactions were considerably slower. The loadings and the conversions of monomers did not affect the M$_n$, all the polymers showed similar M$_n$, approximately 700-800.

The polymerisation of monomer 4.25 using Sn(OBu)$_2$ as the initiator in toluene at 80° C.:

| Run | M:I | [M] | Time/h | % Conv. | M$_n$ (Calc.) | M$_n$ (GPC) | PDI |
|---|---|---|---|---|---|---|---|
| 3 | 27:1 | 1M | 189 | 39 | 980 | 763 | 1.25 |
| 4 | 60:1 | 1M | 119 | 14.0 | 798 | 781 | 1.13 |
| 5 | 70:1 | 0.5M | 119 | 9.8 | 662 | 729 | 1.07 |

EXAMPLE 4

Preparation of a Random Copoly(3Lactide)

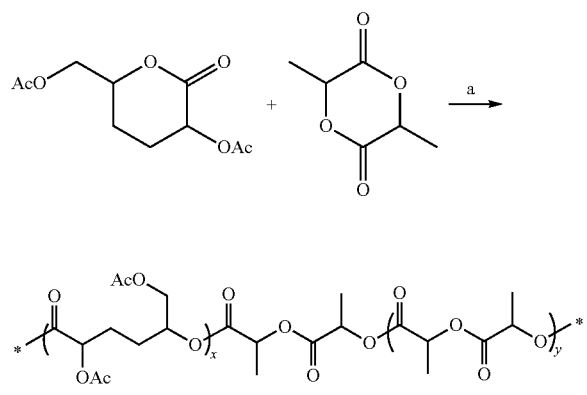

(a) Sn(OBu)$_2$, 80° C., stir, N$_2$

Compound 3 (0.115 g, 0.5 mmol) and L-lactide (0.216 g, 1.5 mmol) were added into an oven dried ampule with a stirrer. Stock solution of Sn(OBu)$_2$ (0.5 mL, 0.04 M in toluene, 0.02 mmol) was added, followed by dried toluene (1.5 mL). The ampule was sealed and heated to 80° C. with stirring. The conversion of compound 3 to polymer reached 80%, and the conversion of L-lactide (which can also be referred to as S-lactide) was about 98% (as judged by $^1$H NMR spectrscopy). The polymerization was quenched by added wet CHCl$_3$ (2 mL) was precipitated in ether. The polymer was purified by the repeated dissolution and precipitation (3×) and dried under vacuum to yield a white solid (0.21 g, 63.4%). $^1$H NMR (400 MHz), δ: 5.0-5.3 (216H, m, OCH(CH$_3$)CO, H-2, H-5); 4.0-4.4 (45 H, m, H-6, H-6'); 2.12-2.22 (62 H, d, COCH$_3$); 2.04-2.12 (68 H, d, COCH$_3$); 1.60-2.05 (101 H, m, H-3, H-3', H-4, H-4'); 1.45-1.60 (590 H, d, CHCH$_3$), 0.91-0.97 (6 H, t, CH$_3$(CH$_2$)$_3$) ppm. GPC(CHCl$_3$, 1 mL/min) M$_n$=10740, PDI=1.38.

EXAMPLE 5

Preparation of Random Copolymer of Compound (3) and S-Lactide Using LZnOEt

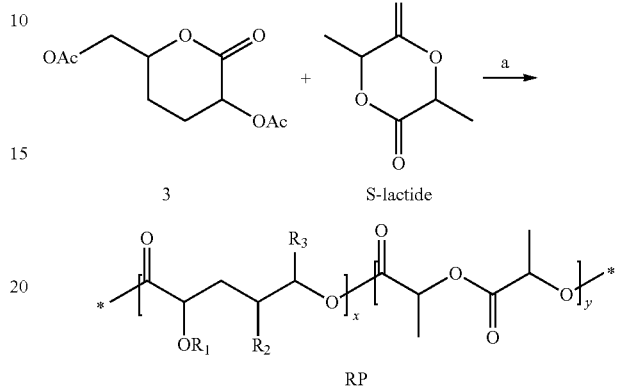

(a) 25° C., THF, LZnOEt (yields, 56%-88%).

Compound 3 (0.115 g, 0.5 mmol) and S-lactide (0.216 g, 1.5 mmol) were added into an oven dried vial, equipped with a stirrer. A stock solution of LZnOEt (0.5 mL, 0.04 M in THF, 0.02 mmol) was added, followed by dried THF (1.5 mL). The solution was stirred, under N$_2$, and quenched after 15 minutes by taking the solution out of the glovebox and by being poured into excess diethyl ether. The purification steps were the same as the experiments using Sn(OBu)$_2$ as the initiator.

The following amounts of compound 3 and 1M S-lactide (LA) stock solution (in THF) and LZnOEt initiator (Zn) stock solution (0.025M) were used in a reaction process as described above to produce the various copolymers RP1, RP2, RP3 and RP4 and PSLA (poly S-lactide):

| Run | Molar Loading of 3:LA:Zn | 3/g | S-LA Stock/ mL | THF/ mL | Zn Stock/ mL | Product/ g | Yield (%) |
|---|---|---|---|---|---|---|---|
| RP1 | 100:200:1 | 0.575 | 5 | 1.5 | 1 | 0.72 | 55.6 |
| RP2 | 50:250:1 | 0.288 | 6.25 | 0.25 | 1 | 0.8 | 67.4 |
| RP3 | 25:275:1 | 0.144 | 6.88 | 0.5 | 1 | 0.87 | 76.7 |
| RP4 | 10:290:1 | 0.058 | 7.37 | 0 | 1 | 0.97 | 88.1 |
| PSLA | 0:300:1 | 0 | 7.5 | 0 | 1 | 0.88 | 81.5 |

Thus, polymers having lactone:lactide loadings in the reaction mixture of 100:200 to 10:290 were produced, although it will be appreciated that copolymers with loadings outside these ranges could also be produced and are encompassed by the invention. The $^1$H NMR spectrum obtained for RP1 was as follows: $^1$H NMR (400 MHz), δ: 4.9-5.6 (m, OCH(CH$_3$)CO, H-2, H-5); 4.0-4.4 (m, H-6, H-6'); 2.12-2.22 (s, COCH$_3$); 2.04-2.12 (m, COCH$_3$); 1.60-2.05 (m, H-3, H-3', H-4, H-4'); 1.45-1.60 (d, CHCH$_3$) ppm. The molecular weight (M$_n$=33850, PDI=1.51) was tested by GPC(CHCl$_3$, 1 mL/min)

The NMR spectrum of the purified copolymer (representative example for RP1 shown in FIG. 14) showed a lower loading of repeat units deriving from 3 than expected on the basis of the reaction stoichiometry, consistent with the relative rates of polymerisation of the monomers and the crude $^1$H NMR spectra. The relative loading of ring opened 3 and S-lactide was calculated by integrating the polymer peaks from 4.0 ppm to 4.5 ppm (due to the 2 protons on C-6 in ring opened 3) and the polymer peaks from 4.9 ppm to 5.5 ppm (due to the 2 methyne protons on each S-lactide unit and H-2 and H-5 in ring opened 3. Table 2 shows the starting ratios of the monomers (3: S-lactide) and the ultimate loading of ring opened 3 in the copolymer.

TABLE 2

Characterisation data for copolymers (P(1 – r – SLA)).

| run | 3:LA:LZnOEt[b] | 1% (M/M)[c] | 1% (w/w)[d] | $M_n$ (GPC)[e] | PDI[f] |
|---|---|---|---|---|---|
| RP1 | 100:200:1 | 17.1 | 24.8 | 33850 | 1.51 |
| RP2 | 50:250:1 | 7.4 | 11.3 | 57380 | 1.59 |
| RP3 | 25:275:1 | 3.8 | 5.9 | 63100 | 1.71 |
| RP4 | 10:290:1 | 0.9 | 1.4 | 95800 | 1.36 |
| PSLA | 0:300:1 | 0 | 0 | 109400 | 1.40 |

[a]Copolymerisation of 3 and S-lactide, initiated by LZnOEt in THF at room temperature, [S-lactide] + [3] = 1M.
[b]The loadings of monomers to initiator.
[c]The molar ratio of the ring opened 3 in the copolymer which is determined by dividing the integration the polymer peaks from 4.0 ppm to 4.5 ppm (ring opened 3, H-6 and H-6') by the polymer peaks from 4.9 ppm to 5.5 ppm (copolymer peaks, two methyne protons on lactide, H-2 and H-5 of ring opened 3).
[d]The weight ratio of the ring opened 1 in the copolymer which is calculated from the molar ratio.
[e]$M_n$ measured by the GPC (CHCl$_3$) using polystyrene standards.
[f]polydispersity indices of the copolymers.

The above process has also been carried out using rac-lactide (mixture of R- and S-lactide). Data for the resulting copolymer, other than for optical properties, was the same as that for the S-lactide copolymer.

Thermal Properties

Differential scanning calorimetry (DSC) and thermal gravimetric analysis (TGA) has been used to characterise the copolymers (RP).

The glass transition temperature of the homopolymer of compound 3, was determined using the Fox and Flory relationship (Fox, T G and Flory, P J, J. Appl. Phys., 21, 581 (1950)). The $T_g(\infty)$ glass transition temperature for infinite molecular weight is 302.8 K, which is 29.6° C. The homopolymer is completely amorphous and has no melting temperature.

The glass transition temperatures of copolymers obey the Fox Equation:

$$\frac{1}{T_g} = \frac{w_a}{T_{g,a}} + \frac{w_b}{T_{g,b}}$$

where $T_{g,a}$ is the glass transition temperature of homopolymer a; $T_{g,b}$ is the glass transition temperature of homopolymer b; $w_a$ is the weight fraction of monomer a; $w_b$ is the weight fraction of monomer b. In this case, homopolymer a is a homopolymer of compound 3, and $T_{g,a}(\infty)$ is 29.6° C. (302.8 K); homopolymer b is PSLA, and $T_{g,b}(\infty)$ is 57.8° C. (331.1 K)—the $T_{g,b}(\infty)$ was determined by measuring the PSLA homopolymer (monomer:initiator, 300:1) under the same conditions as for the copolymers, the value agrees well with literature values for PSLA $T_g$.

TABLE 3

The $T_g$ measured by DSC and the $T_g$ calculated from the Fox equation for the random copolymers RP(1-SLA).[a]

| Copolymer | 1% (w/w) | $T_g$ Calc. (° C.)[b] | $T_g$ (° C.)[c] | $T_m$ (° C.)[d] |
|---|---|---|---|---|
| RP1 | 24.8 | 46.8 | 46.0 | N |
| RP2 | 11.3 | 52.2 | 52.2 | 155.7 (145.0) |
| RP3 | 5.9 | 54.7 | 53.7 | 160.5 (151.4) |
| RP4 | 1.4 | 57.0 | 55.1 | 167.2 |

[a]The DSC measurement was measured in three heating and cooling cycles. The samples were heated to 200° C. at 10° C./min and cooled to –40° C. at 10° C./min. The second and third cycle gave the same spectrum. The data was from the second heating cycle.
[b]The $T_g$ is calculated from the Fox equation for the random copolymers RP(1-LA);
[c]The measured $T_g$ for the copolymer.
[d]The measured $T_m$ (melting temperature) for the copolymer.

The random copolymers described above incorporate up to 25% by weight of a carbohydrate lactone together with S-LA. The loading of the carbohydrate lactone into the copolymers can be estimated by integration of the NMR spectrum. The molecular numbers vary from 10,000-100,000, as estimated by GPC. These copolymers show tunable glass transition temperatures in the range 30° C.-60° C. depending on the loading of carbohydrate lactone monomer. At low loadings it is believed that microphase separation occurs as a melting temperature for the S-LA blocks is still observed. When loading of carbohydrate lactone exceeds 20% the copolymers are completely amorphous materials. The carbohydrate lactone modifies the degradation rate of the copolymers; as the carbohydrate portion increases so the degradation rate increases. This relates to two factors; 1) the reduced glass transition temperature and decreased crystallinity and 2) the increased hydrophilicty.

Degradation of the Copolymers

Incorporation of carbohydrates into aliphatic polyesters acts to modify degradation rates. It is well known that PSLA is slow to degrade and this can be problematic for certain applications. Furthermore, solid samples of PLA (e.g. for packaging or bulk biomedical applications) need to be above the glass transition temperature (56° C.) in order for the degradation to proceed at all. This creates some significant problems for PLA application and marketing as degradation will only actually occur in industrial composting conditions and not using domestic composting. For biological applications there are also applications for which faster PLA degradation could be beneficial.

The incorporation of 3 into copolymers with S-lactide increases the degradation rate compared to polylactide, as it increases the hydrophilicity (water uptake) of the material. Furthermore, the copolymers have decreased $T_g$ and $T_m$ versus PSLA which will further facilitate water uptake and increase the degradation rate. Degradation of RP1-RP4 and PSLA was monitored using GPC as this enabled in situ determination of the change of $M_n$ of the samples and also gave a clear indication of complete consumption of the copolymer. The copolymers were dissolved in THF and phosphate buffered saline solution (PBS, 24 mM Na$_2$HPO$_4$ and 16 mM KH$_2$PO$_4$ in 0.9% NaCl, pH=7.4, 0.1 mL) was added to the samples. The samples were regularly monitored by GPC.

The degradation of PLA (polylactide). can be accomplished under neutral conditions which simulate the environment in vivo, by dissolving the PLA in a suitable organic solvent and addition of water. To ensure that an autocatalytic mechanism does not occur (as the degradation product itself is acidic) PBS buffer is added. Liu et al. showed that for PLA the number-average degree of polymerisation at time t ($X_t$) can be related to the starting degree of polymerisation ($X_0$), the time and the degradation rate constant ($k_x$) according to Equation 3 (Liu et al, Polym. Degrad. Stab. 2006, 91, 3259-3265).

$$\ln\frac{X_t-1}{X_t} = \ln\frac{X_0-1}{X_0} - k_x t \qquad \text{Equation 3}$$

Where $X_0$ is the number-average degree of polymerisation of polymer at the initial time; $X_t$ is the number-average degree of polymerisation at time t; $k_x$ is the degradation rate constant.

Using Equation 3, plots of $\ln\{(X_t-1)/X_t\}$ versus time were made for the various copolymers and the linear gradients used to determine $-k_x$.

TABLE 4

The degradation of the copolymers.

| run | Loading[a] 3:LA:LZnOEt | 1%[b] (M/M) | 1%[c] (w/w) | $M_n$[d] (GPC) | PDI | $k_x$[e]/$-10^{-4}$ | $R^2$ |
|---|---|---|---|---|---|---|---|
| RP1 | 100:200:1 | 17.1 | 24.8 | 33850 | 1.51 | 4.2 | 0.98 |
| RP2 | 50:250:1 | 7.4 | 11.3 | 57380 | 1.59 | 3.1 | 0.99 |
| RP3 | 25:275:1 | 3.8 | 5.9 | 63100 | 1.71 | 2.4 | 0.99 |
| RP4 | 10:290:1 | 0.9 | 1.4 | 95800 | 1.36 | 1.3 | 0.99 |
| PSLA | 0:300:1 | 0 | 0 | 109400 | 1.40 | 1.0 | 0.99 |

[a]The loadings of monomers to initiator used in the ROP.
[b]The molar ratio of the ring opened 3 in the copolymer, which is determined by dividing the integration the polymer peaks from 4.0 ppm to 4.5 ppm (ring opened 3, H-6 and H-6') by the polymer peaks from 4.9 ppm to 5.5 ppm (copolymer peaks, two methyne protons on lactide, H-2 and H-5 of ring opened 3).
[c]The weight ratio of the ring opened 3 in the copolymer which is calculated from the molar ratio.
[d]$M_n$ measured by the GPC (CHCl$_3$) using polystyrene as the standard.
[e]$k_x$ from gradients.

As the quantity of 3 in the co-polymer increases (going from polymer RP4 to RP1), so the degradation rate increases. The homopolymer of S-lactide (PSLA) has the slowest degradation rate. This ability to control the degradation of the copolymer by changing the compositions has a range of potential uses, for example in drug delivery/controlled release there is a need to develop more rapidly degradable excipients than PLA.

It should be appreciated that various changes and modifications to the presently preferred embodiments described herein will be apparent to those skilled in the art. Such changes and modifications, which can be made without departing from the spirit and scope of the invention, fall within the scope of the invention.

The invention claimed is:

1. A polymer formed from monomers of formula (I)

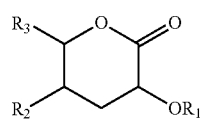

(I)

wherein $R_1$ is selected from hydrogen, acyl, ester, heteroaryl, alkylheteroaryl, silyl, sulfonyl, a drug molecule or a peptide;
$R_2$ is hydrogen or $OR_{1'}$; and
$R_3$ is methyl or —$CH_2OR_{1''}$;
wherein $R_{1'}$ and $R_{1''}$ are both as defined for $R_1$, each occurrence of $R_1$, $R_{1'}$ and $R_{1''}$ may be the same or different.

2. The polymer of claim 1, wherein a) $R_2$ is hydrogen and $R_3$ is —$CH_2OR_{1''}$ or methyl; or b) $R_2$ is $OR_{1'}$ and $R_3$ is —$CH_2OR_{1''}$.

3. The polymer of claim 1, wherein $R_1$, $R_{1'}$ and $R_{1''}$ where present, are acyl.

4. The compound of claim 3, wherein $R_1$, $R_{1'}$ and $R_{1''}$ where present, are —$C(O)CH_3$.

5. The polymer of claim 1, wherein the polymer comprises a mixture of a cyclic polymer and a linear polymer, wherein the cyclic and linear polymers have the structures set out below:

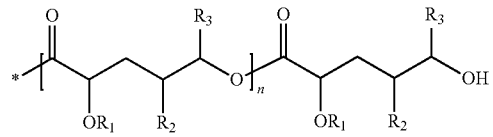

-continued

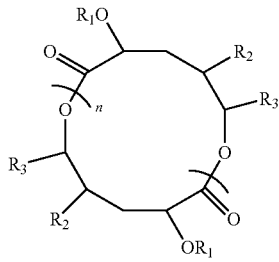

wherein n is between 1 and 60 and wherein termination of the linear polymer (*) is OH or OR, wherein R is alkyl or alkylaryl.

6. The polymer of claim 1, wherein the polymer is a cyclic polymer having the structure:

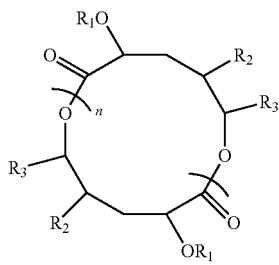

wherein n is between 1 and 60.

7. The polymer of claim 1, wherein the polymer is a copolymer formed from a lactone compound of formula (I) and a second lactone or a cyclic carbonate.

8. The polymer of claim 7, wherein the second lactone is selected from lactide, glycolide, caprolactone, valerolactone, butyrolactone and the cyclic carbonate is trimethylene carbonate.

9. The polymer of claim 7 wherein the polymer is a copolymer represented by the structure:

wherein the mole fraction of x within the copolymer is between 0.5% and 20% and the mole fraction of y is between 80% and 99.5%.

10. The polymer of claim 7, wherein the polymer is a random copolymer.

11. The polymer of claim 1, wherein the polymer is a graft copolymer comprising a polymer backbone formed from polymerization of a lactone compound of formula (I) and a second polymer bonded to functional groups present on the lactone compound.

12. A process for the polymerization of a lactone compound of formula (I) as defined in claim 1, wherein the process comprises exposing a lactone compound of formula (I) to a metal initiator and allowing a ring opening polymerization reaction to occur.

13. The process of claim 12, wherein the initiator is a Lewis acidic metal alkoxide complex selected from the group consisting of, but not limited to, tin initiators, including tin(II) alkoxide complexes and tin(II) carboxylate complexes+alcohols (e.g. Sn(II)octanoate and two equivalents of an alcohol or one equivalent of a diol group (e.g. methanol, benzyl alcohol, butanediol) or $Sn(OBu)_2$); zinc alkoxide complexes (including complexes with a ligand and without a ligand (homoleptic complexes); aluminium alkoxide complexes; titanium alkoxide complexes; zirconium alkoxide complexes; alkali earth alkoxide complexes; yttrium alkoxide complexes; lanthanum alkoxide complexes; and calcium alkoxide complexes.

14. The process of claim 13, wherein the initiator is a tin alkoxide initiator of formula $Sn(OR)_2$ or a zinc alkoxide complex of formula LZnOR, wherein R is alkyl or alkylaryl and L is a zinc co-ordinating ligand.

15. The process of claim 14, wherein the zinc alkoxide complex comprises a zinc-coordinating ligand of formula (L):

wherein $R^a$ is hydrogen, alkyl, alkoxy, a halogen, $NO_2$, $NH_2$, alkylamine or dialkylamine; and each $R^b$ is independently hydrogen, alkyl, alkylaryl or aryl.

16. The process of claim 15, wherein $R^a$ is tBu and each occurrence of $R^b$ is Me.

17. The process of claim 15, wherein the initiator is a zinc ethoxide complex having the formula LZnOEt.

18. The process of claim 12, wherein the polymerization is performed under mild conditions, namely with 0.5M-2M concentration of lactone compound in a chlorinated solvent, an ether solvent or an aromatic solvent at a temperature of 25-100° C. or where the polymerization is carried out at 25-100° C. with no solvent present.

19. The process of claim 12, wherein the process comprises providing a mixture of a lactone compound of formula (I) with a second lactone compound or a cyclic carbonate, exposing the mixture to a metal initiator and allowing a ring opening polymerization reaction to occur to produce a random copolymer.

20. The process of claim 12, wherein the process comprises exposing a lactone compound of formula (I) to a metal initiator and allowing a ring opening polymerization reaction to occur followed by addition of a second lactone compound or a cyclic carbonate, to produce a block copolymer.

21. A polymer as produced by the process of claim 12.

22. A polymer as defined in claim 1 for the production of a biomaterial, for use as a packaging material, for the manufacture of fibres, for the manufacture of a medical device including degradable sutures, dressings, stent and implants, for the manufacture of a matrix for tissue engineering or as an excipient for drug delivery, for use as an impact modifier for a biodegradable packaging material.

23. A packaging material, a medical device or an excipient for drug delivery comprising a polymer as defined in claim 1.

24. The polymer of claim 1, wherein $R_1$ is acyl; $R_2$ is hydrogen; and $R_3$ is —$CH_2OR_{1''}$, wherein $R_{1''}$ is acyl.

25. A polymer formed from monomers of formula (I)

wherein $R_1$ is selected from hydrogen, alkyl, haloalkyl, acyl, ester, aryl, heteroaryl, alkylaryl, alkylheteroaryl, silyl, sulfonyl, a drug molecule or a peptide;
$R_2$ is hydrogen or $OR_{1'}$; and
$R_3$ is methyl or —$CH_2OR_{1''}$;
wherein $R_{1'}$, and $R_{1''}$ are both as defined for $R_1$, each occurrence of $R_1$, $R_{1'}$ and $R_{1''}$ may be the same or different,
wherein the polymer comprises a mixture of a cyclic polymer and a linear polymer,
wherein the cyclic and linear polymers have the structures set out below:

-continued

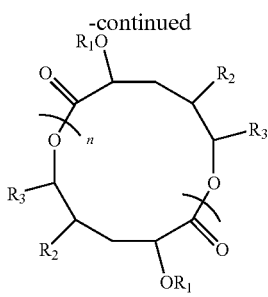

wherein n is between 1 and 60 and wherein termination of the linear polymer (*) is OH or OR wherein R is alkyl or alkylaryl.

26. A polymer formed from monomers of formula (I)

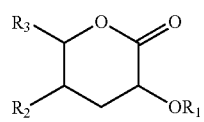

wherein $R_1$ is selected from hydrogen, alkyl, haloalkyl, acyl, ester, aryl, heteroaryl, alkylaryl, alkylheteroaryl, silyl, sulfonyl, a drug molecule or a peptide;
$R_2$ is hydrogen or $OR_{1'}$; and
$R_3$ is methyl or —$CH_2OR_{1''}$;
wherein $R_{1'}$ and $R_{1''}$ are both as defined for $R_1$, each occurrence of $R_1$, $R_{1'}$ and $R_{1''}$ may be the same or different,
wherein the polymer is a cyclic polymer having the structure:

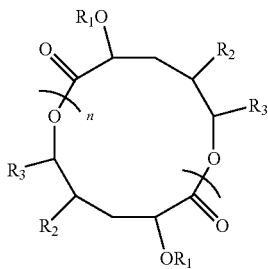

wherein n is between 1 and 60.

27. A polymer formed from monomers of formula (I)

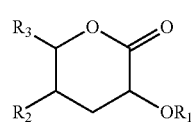

wherein $R_1$ is selected from hydrogen, alkyl, haloalkyl, acyl, ester, aryl, heteroaryl, alkylaryl, alkylheteroaryl, silyl, sulfonyl, a drug molecule or a peptide;
$R_2$ is hydrogen or $OR_{1'}$; and
$R_3$ is methyl or —$CH_2OR_{1''}$;
wherein $R_{1'}$ and $R_{1''}$ are both as defined for $R_1$, each occurrence of $R_1$, $R_{1'}$ and $R_{1''}$ may be the same or different,
wherein the polymer is a copolymer represented by the structure:

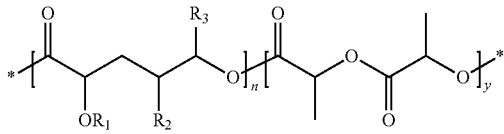

wherein the mole fraction of x within the copolymer is between 0.5% and 20% and the mole fraction of y is between 80% and 99.5%.

28. The polymer of claim 1, wherein $R_1$ is —$C(O)CH_3$, $R_2$ is hydrogen, $R_3$ is —$CH_2OR_{1''}$, and $R_{1''}$ is —$C(O)CH_3$.

29. The polymer of claim 25, wherein $R_1$ is —$C(O)CH_3$, $R_2$ is hydrogen, $R_3$ is —$CH_2OR_{1''}$, and $R_{1''}$ is —$C(O)CH_3$.

30. The polymer of claim 26, wherein $R_1$ is —$C(O)CH_3$, $R_2$ is hydrogen, $R_3$ is —$CH_2OR_{1''}$, and $R_{1''}$ is —$C(O)CH_3$.

31. The polymer of claim 27, wherein $R_1$ is —$C(O)CH_3$, $R_2$ is hydrogen, $R_3$ is —$CH_2OR_{1''}$, and $R_{1''}$ is —$C(O)CH_3$.

32. The polymer of claim 7, wherein the molar ratio of lactone monomer of formula (I):second lactone or cyclic carbonate is from 1:1 to 1:1000.

33. The polymer of claim 8, wherein the molar ratio of lactone monomer of formula (I):second lactone or cyclic carbonate is from 1:1 to 1:1000.

* * * * *